US012569662B2

(12) United States Patent
Kakinoki et al.

(10) Patent No.: US 12,569,662 B2
(45) Date of Patent: *Mar. 10, 2026

(54) MEDICAL CONNECTOR

(71) Applicant: TERUMO KABUSHIKI KAISHA, Tokyo (JP)

(72) Inventors: Toshihiko Kakinoki, Oyama (JP); Kazuya Akiyama, Nakakoma-gun (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 270 days.

This patent is subject to a terminal disclaimer.

(21) Appl. No.: 18/348,855

(22) Filed: Jul. 7, 2023

(65) Prior Publication Data

US 2023/0355947 A1 Nov. 9, 2023

Related U.S. Application Data

(63) Continuation of application No. 16/910,779, filed on Jun. 24, 2020, now Pat. No. 11,738,189, which is a (Continued)

(30) Foreign Application Priority Data

Dec. 26, 2017 (JP) ................................. 2017-250127
Oct. 17, 2018 (JP) ................................. 2018-196068

(51) Int. Cl.
*A61M 39/10* (2006.01)
*A61M 39/24* (2006.01)

(52) U.S. Cl.
CPC ........ *A61M 39/1011* (2013.01); *A61M 39/10* (2013.01); *A61M 39/24* (2013.01); *A61M 2039/2426* (2013.01)

(58) Field of Classification Search
CPC .............. A61M 39/1011; A61M 39/24; A61M 2039/2426; A61M 2039/1077;
(Continued)

(56) References Cited

U.S. PATENT DOCUMENTS 6,402,207 B1 6/2002 Segal et al.
2002/0193752 A1 12/2002 Lynn
(Continued)

FOREIGN PATENT DOCUMENTS

EP 2 712 652 A2 4/2014
JP 2001-187990 A 7/2001
(Continued)

OTHER PUBLICATIONS

Extended European Search Report issued in corresponding European Patent Application No. 18896936.4, dated Jul. 2, 2020.
(Continued)

*Primary Examiner* — Lauren P Farrar
(74) *Attorney, Agent, or Firm* — Foley & Lardner LLP

(57) ABSTRACT

A medical connector includes: a first connection section that defines a first passage, the first connection section comprising a first tubular portion; a second connection section that defines a second passage communicating with the first passage, the second connection section comprising a second tubular portion inserted into the first tubular portion; and a rotation control section that controls relative rotation of the first connection section and the second connection section in a connection state.

11 Claims, 16 Drawing Sheets

Related U.S. Application Data continuation of application No. PCT/JP2018/042333, filed on Nov. 15, 2018.

(58) Field of Classification Search

CPC .. A61M 2039/1033; A61M 2039/1072; A61M 39/10

See application file for complete search history.

(56)                     References Cited

U.S. PATENT DOCUMENTS

| | | |
|---|---|---|
| 2006/0189961 A1 | 8/2006 | Miyahara |
| 2007/0088327 A1 | 4/2007 | Guala |
| 2008/0172039 A1 | 7/2008 | Raines |
| 2011/0137294 A1 | 6/2011 | Calimeri et al. |
| 2013/0187381 A1 | 7/2013 | Guala |
| 2017/0036008 A1* | 2/2017 | Tsai .................. A61M 39/1011 |

FOREIGN PATENT DOCUMENTS

| | | |
|---|---|---|
| JP | 2009-011820 A | 1/2009 |
| JP | 2016-519979 A | 7/2016 |
| JP | 2017-515544 A | 6/2017 |

OTHER PUBLICATIONS

International Searching Authority, "International Search Report," issued in connection with International Patent Application No. PCT/JP2018/042333, dated Dec. 11, 2018.

International Searching Authority, "Written Opinion," issued in connection with International Patent Application No. PCT/JP2018/042333, dated Dec. 11, 2018.

Office Action issued in corresponding Chinese Patent Application No. 201880075080.3, dated Dec. 1, 2021.

\* cited by examiner

MEDICAL CONNECTOR

CROSS-REFERENCE TO RELATED APPLICATIONS

This is a continuation of U.S. application Ser. No. 16/910,779, filed on Jun. 24, 2020, which is a bypass continuation of PCT Application No. PCT/JP2018/042333, filed on Nov. 15, 2018, which claims priority to Japanese Application Nos. 2017-250127, filed on Dec. 26, 2017, and 2018-196068, filed on Oct. 17, 2018. The contents of these applications are hereby incorporated by reference in their entireties.

BACKGROUND

The present disclosure relates to a medical connector.

Conventionally, when an infusion, blood transfusion, artificial dialysis, or the like is performed, an infusion line is formed using a medical tube or the like, and a liquid such as a medicinal solution is supplied into a body through the infusion line. Medical devices such as the medical tube and a syringe used in the infusion line can be connected to each other using a medical connector.

JP 2009-011820 A discloses, as a medical connector of this type, a configuration in which a screw portion that can be screwed with a luer lock connector is provided on an outer peripheral face of a housing.

SUMMARY

When a medical connector having a screw portion as in the medical connector described in JP 2009-011820 A is used, a connection state between the medical connector and a medical device can be stably maintained. However, there is still a possibility of rotation in a direction that loosens a screwing state of the screw portion as an unintended external force such as a twist of a medical tube is applied.

The present disclosure aims to provide a medical connector having a configuration that can easily maintain a connection state with a medical device.

A medical connector as a first aspect of the present disclosure includes: a first connection section that defines a first passage; a second connection section that defines a second passage communicating with the first passage; and a rotation control section that controls relative rotation of the first connection section and the second connection section in a connection state. The second connection section includes a wall face that abuts on the first connection section to restrict the first connection section from moving in a direction to be separated from the second connection section along an axis of the first passage and the second passage. The rotation control section allows the second connection section to rotate relative to the first connection section in a first circumferential direction about the axis as a central axis and restricts the second connection section from rotating relative to the first connection section in a second circumferential direction opposite to the first circumferential direction, in a state in which the first connection section abuts on the wall face. The first connection section is connectable to a first medical device using a rotating operation in the second circumferential direction and is disconnectable from the first medical device using a rotating operation in the first circumferential direction.

In one embodiment of the present disclosure, the first connection section includes a male screw portion that is screwable with a female screw portion of the first medical device, and the male screw portion is screwed with the female screw portion of the first medical device by being rotated in the second circumferential direction relative to the female screw portion of the first medical device.

In one embodiment of the present disclosure, when the other medical device is a first medical device, the second connection section is connectable to a second medical device using a rotating operation in the first circumferential direction and is disconnectable from the second other medical device using a rotating operation in the second circumferential direction.

In one embodiment of the present disclosure, the second connection section includes a female screw portion that is screwable with a male screw portion of the second medical device, and the female screw portion is screwed with the male screw portion of the second medical device by being rotated in the first circumferential direction relative to the male screw portion of the second medical device.

In one embodiment of the present disclosure, the rotation control section includes a ratchet mechanism formed of a first housing constituting at least a part of the first connection section, and a second housing constituting at least a part of the second connection section.

In one embodiment of the present disclosure, in a first tubular portion of one connection section of the first connection section and the second connection section, a second tubular portion of the other connection section is inserted. An inner wall of the first tubular portion and an outer wall of the second tubular portion form an abutment region in each part of the first tubular portion and the second tubular portion along an axial direction in an insertion region where the first tubular portion and the second tubular portion overlap in a radial direction. The second connection section rotates in the first circumferential direction relative to the first connection section while sliding with respect to the first connection section in the abutment region.

In one embodiment of the present disclosure, the abutment region is formed over an entire circumferential region of the first tubular portion and the second tubular portion.

In one embodiment of the present disclosure, an annular groove is formed on an outer wall of the first tubular portion of the one connection section, and the other connection section includes a claw portion that is located outside the first tubular portion of the one connection section in the radial direction and fits into the annular groove. The wall face is constituted by a groove wall of the annular groove or an outer wall of the claw portion.

In one embodiment of the present disclosure, when the wall face is a first wall face, the second connection section includes a second wall face that abuts on the first connection section to restrict the first connection section from moving in a direction to approach the second connection section along the axis. The rotation control section allows the second connection section to rotate relative to the first connection section in the first circumferential direction and restricts the second connection section from rotating relative to the first connection section in the second circumferential direction, in a state in which the first connection section abuts on the second wall face.

In one embodiment of the present disclosure, at least a part of the first connection section is constituted by a valve body that closes the first passage.

According to the present disclosure, it is possible to provide the medical connector having the configuration that can easily maintain the connection state with the medical device.

DETAILED DESCRIPTION

Hereinafter, an embodiment of a medical connector according to the present disclosure will be described with reference to FIGS. 1 to 17. The same reference signs are attached to members and portions common in the respective drawings.

Figure 1:
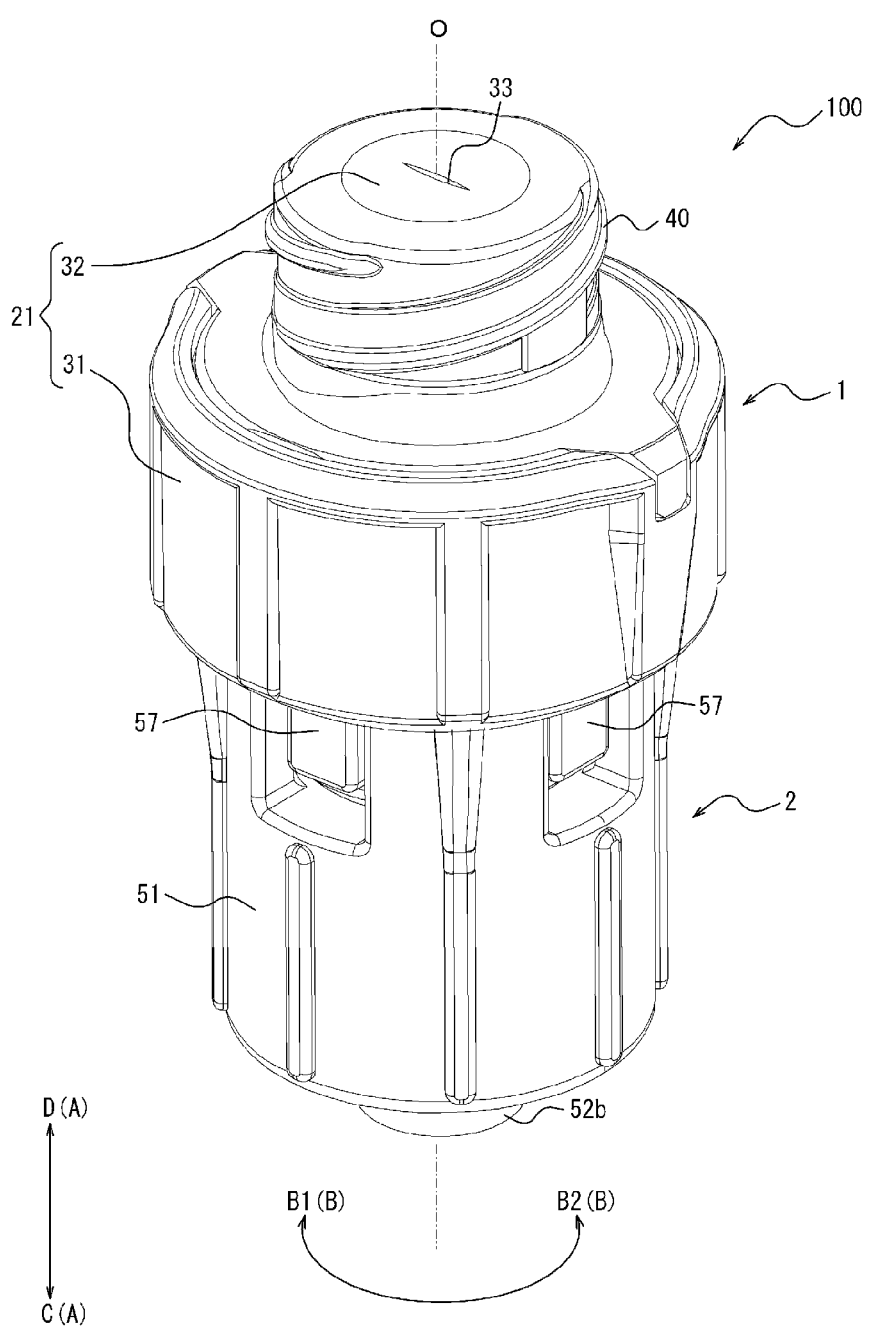
FIG. 1 is a perspective view illustrating a medical connector as one embodiment.
Figure 2:
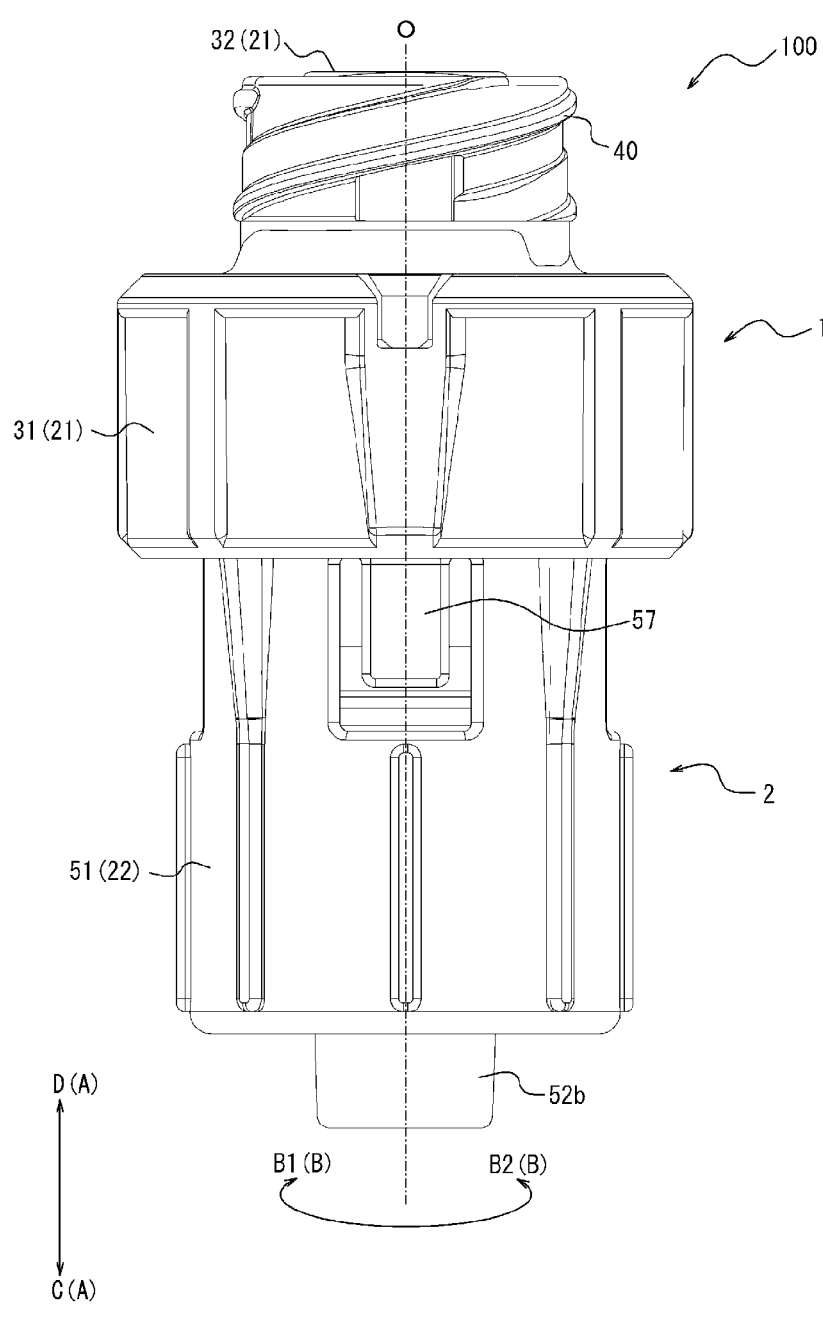
FIG. 2 is a side view of the medical connector illustrated in FIG. 1 as viewed from a side surface.
Figure 3:
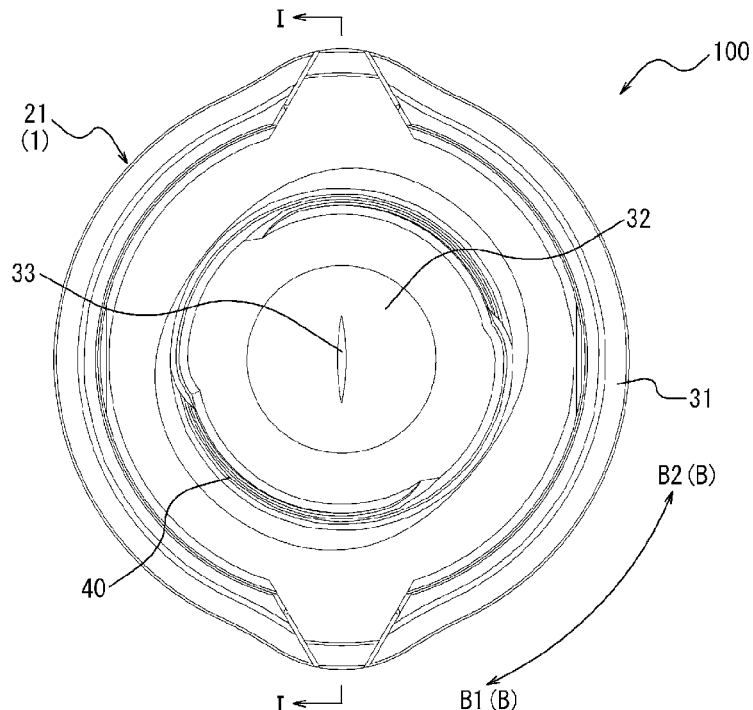
FIG. 3 is a top view of the medical connector illustrated in FIG. 1 as viewed from a top surface.
Figure 4:
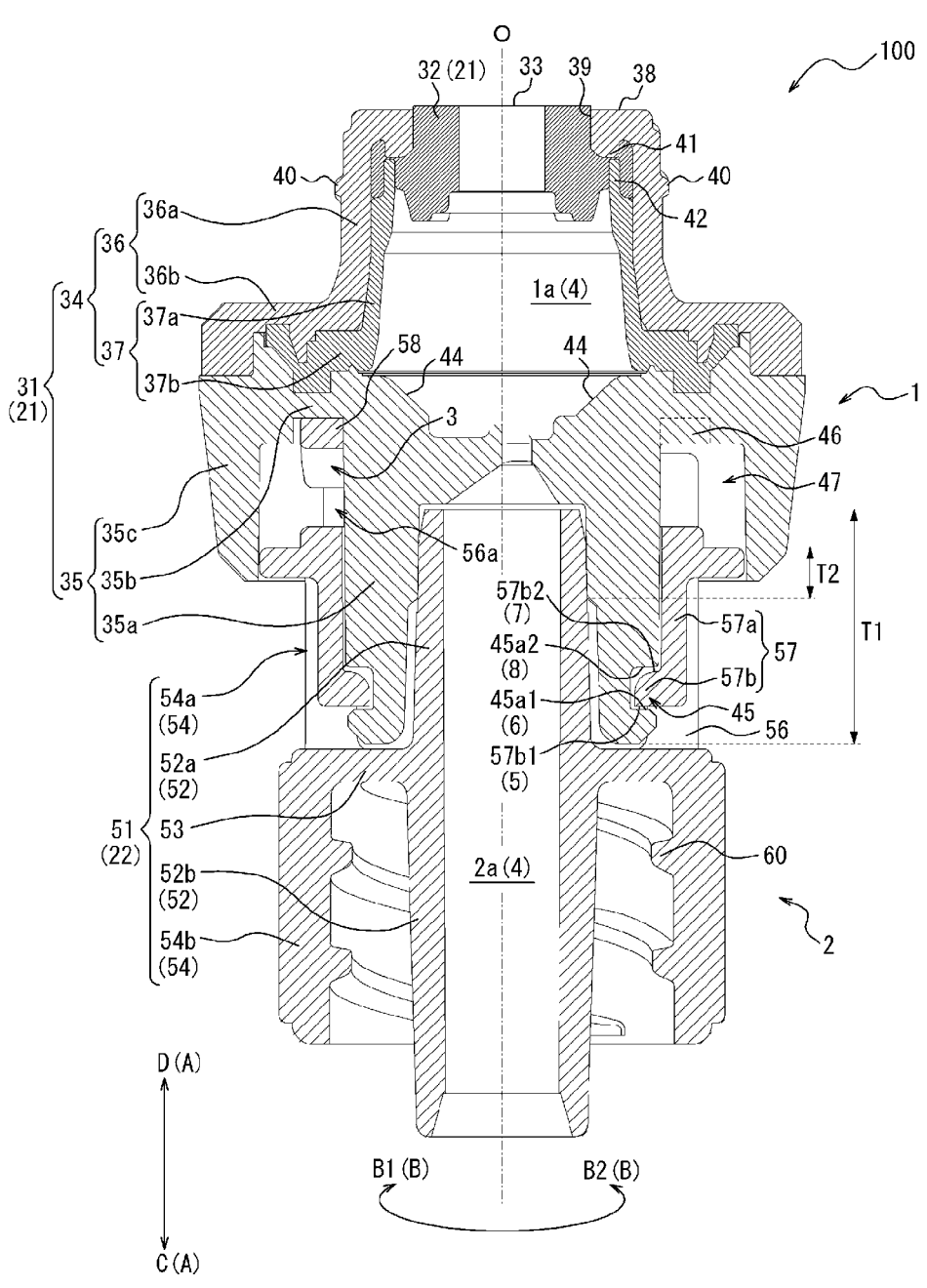
FIG. 4 is a cross-sectional view of a cross section taken along line I-I of FIG. 3.

FIG. 1 is a perspective view illustrating a medical connector 100 according to the present embodiment. FIG. 2 is a side view of the medical connector 100 illustrated in FIG. 1 as viewed from a side surface. FIG. 3 is a top view of the medical connector 100 illustrated in FIG. 1 as viewed from a top surface. FIG. 4 is a cross-sectional view illustrating a cross section taken along line I-I of FIG. 3.

As illustrated in FIGS. 1 to 4, the medical connector 100 includes a first connection section 1, a second connection section 2, and a rotation control section 3. The rotation control section 3 controls relative rotation of the first connection section 1 and the second connection section 2 in a connection state.

More specifically, a part of the first connection section 1 is constituted by a first housing 31 in the medical connector 100 of the present embodiment. Further, a part of the second connection section 2 is constituted by a second housing 51 in the medical connector 100 of the present embodiment. A rotation control section 3 of the present embodiment includes a ratchet mechanism formed by the first housing 31 and the second housing 51. Detailed configurations of the first housing 31, the second housing 51, and the ratchet mechanism formed by the first housing 31 and the second housing 51 will be described below.

As illustrated in FIG. 4, the first connection section 1 defines a first passage 1a. The second connection section 2 is connected to the first connection section 1. The second connection section 2 defines a second passage 2a communicating with the first passage 1a. In other words, the medical connector 100 defines a connector passage 4 including the first passage 1a and the second passage 2a. An axis O of the first passage 1a and the second passage 2a forms an axis of the connector passage 4.

Each of the first connection section 1 and the second connection section 2 are connectable to medical devices using a rotating operation. Further, each of the first connection section 1 and the second connection section 2 are disconnectable from the medical devices using a rotating operation. The "medical devices" are not particularly limited, and examples thereof include a medical connector different from the medical connector 100, a medical tube, a syringe, and the like. Hereinafter, a medical device that can be connected to the first connection section 1 is referred to as a "first medical device" for convenience of description. Hereinafter, a medical device that can be connected to the second connection section 2 is referred to as a "second medical device" for convenience of description.

The expression of "connected to medical devices using a rotational operation" means that some or all of connection processes for achieving a liquid-tight connection state with the medical devices include the rotating operation with respect to the medical devices. Further, the expression of "disconnectable from medical devices using a rotating operation" means that some or all of disconnection processes for releasing a liquid-tight connection state with the medical devices include the rotating operation with respect to the medical devices.

Although details will be described below, the first connection section 1 of the present embodiment can be connected to the first medical device by screw connection (hereinafter, sometimes referred to as "screwing") using a rotating operation. The first connection section 1 of the present embodiment can be disconnected from the first medical device using a rotating operation in a direction opposite to that at the time of connection. Further, the second connection section 2 of the present embodiment can be connected to a second medical device by screw connection using a rotating operation. The second connection section 2 of the present embodiment can be disconnected from the second medical device using a rotating operation in a direction opposite to that at the time of connection. In other words, the medical connector 100 of the present embodiment is an example in which the rotating operation with respect to the medical device is used in all of the connection processes and the disconnection processes.

In this manner, each of the first connection section 1 and the second connection section 2 in the connection state is configured to be connectable to and disconnectable from medical devices using the rotating operation. Therefore, for example, when a medical tube as an example of the first medical device is connected to the first connection section 1 and another medical tube as an example of the second medical device is connected to the second connection section 2, passages of the two medical tubes can be made in fluid communication via the connector passage 4 of the medical connector 100.

In the medical connector 100, the first connection section 1 and the second connection section 2 are restricted from moving along the axis O in directions to be separated from each other. Therefore, even if one of the first connection section 1 and the second connection section 2 is moved relative to the other so as to be separated in an axial direction A along the axis O, it is difficult to separate the both. That is, the first connection section 1 and the second connection section 2 are configured so as not to be separated from each other in the movement in the separating directions along the axial direction A. In other words, when focusing on an arbitrary predetermined point of the first connection section 1 and an arbitrary predetermined point of the second connection section 2, a distance between these two predetermined points in the axial direction A is set so as not to exceed a predetermined distance. Such a configuration can be achieved by providing the first connection section 1 and the second connection section 2 with portions that are arranged while overlapping in the axial direction A and abut on each other to interfere when the first connection section 1 and the second connection section 2 try to separate in the axial A direction A.

Specifically, the second connection section 2 includes a wall face 5. This wall face 5 abuts on the first connection section 1 to restrict the first connection section 1 from moving in a direction to be separated from the second connection section 2 along the axis O of the first passage 1*a* and the second passage 2*a*. Further, the first connection section 1 includes a wall face 6. This wall face 6 abuts on the wall face 5 of the second connection section 2 to restrict the second connection section 2 from moving in a direction to be separated from the first connection section 1 along the axis O of the first passage 1*a* and the second passage 2*a*. More specifically, the wall face 6 of the first connection section 1 and the wall face 5 of the second connection section 2 oppose each other in the axial direction A. When the first connection section 1 and the second connection section 2 are to separate in the axial direction A, the wall face 6 of the first connection section 1 and the wall face 5 of the second connection section 2 come into contact with each other. Accordingly, the separation movement in the axial direction A of the first connection section 1 and the second connection section 2 is restricted. Details of the wall face 6 of the first connection section 1 and the wall face 5 of the second connection section 2 in the present embodiment will be described below (see FIG. 4 and the like).

The rotation control section 3 allows the second connection section 2 to rotate relative to the first connection section 1 in a first circumferential direction B1 about the axis O as a center axis in a state in which the first connection section 1 and the second connection section 2 are restricted from moving in the directions to be separated from each other along the axis O (hereinafter, sometimes referred to as a "separation-restricted state"). Further, the rotation control section 3 restricts the second connection section 2 from rotating relative to the first connection section 1 in a second circumferential direction B2 opposite to the first circumferential direction B1 in the separation-restricted state. The separation-restricted state in the present embodiment is a state in which the wall face 6 of the first connection section 1 abuts on the wall face 5 of the second connection section 2 as described above.

That is, the rotation control section 3 allows the second connection section 2 to rotate relative to the first connection section 1 in one direction (the first circumferential direction B1) of a circumferential direction B in the above-described separation-restricted state. On the other hand, the rotation control section 3 restricts the second connection section 2 from rotating relative to the first connection section 1 in the opposite direction (the second circumferential direction B2) of the circumferential direction B in the above-described separation-restricted state. Details of the configuration of the rotation control section 3 of the present embodiment will be described below (see FIGS. 5 to 11 and the like).

As described above, the first connection section 1 can be connected to the first medical device using a rotating operation and can be disconnected from the first medical device using a rotating operation. More specifically, the first connection section 1 can be connected to the first medical device using the rotating operation in the second circumferential direction B2. Further, the first connection section 1 can be disconnected from the first medical device using the rotating operation in the first circumferential direction B1.

Because the medical connector 100 includes the above-described rotation control section 3 and the first connection section 1 that can be connected to and disconnected from the first medical device in the above-described rotation directions, the first medical device connected to the medical connector 100 is less likely to come off the medical connector 100 as compared with a configuration that does not include the above-described rotation control section 3.

That is, when the second connection section 2 tries to rotate in the first circumferential direction B1, this rotational torque is used by the rotation control section 3 for the rotating operation between the first connection section 1 and the second connection section 2. Accordingly, it is difficult for the above-described rotational torque to act on a connecting portion between the first connection section 1 and the first medical device. Therefore, it becomes difficult for the first connection section 1 to rotate in the first circumferential direction B1 relative to the first medical device. In this manner, even if an external force that tries to release the connection state between the first connection section 1 and the first medical device acts on a position of the second connection section 2, this external force can be suppressed from acting on the connecting portion between the first connection section 1 and the first medical device by the rotation control section 3. Therefore, it is possible to prevent the connection state between the medical connector 100 and the first medical device from being unintentionally released. As a result, it is possible to realize a configuration in which the connection state between the medical connector 100 and the first medical device is easily maintained.

As described above, the second connection section 2 of the present embodiment can be also connected to the second medical device using a rotating operation, and can be disconnected from the second medical device using a rotating operation. More specifically, the second connection section 2 of the present embodiment can be connected to the second medical device using the rotating operation in the first circumferential direction B1. Further, the second connection section 2 of the present embodiment can be disconnected from the second medical device using the rotating operation in the second circumferential direction B2.

Because the medical connector 100 of the present embodiment includes the above-described rotation control section 3 and the second connection section 2 that can be connected to and disconnected from the second medical device in the above-described rotation directions, the second medical device connected to the medical connector 100 is less likely to come off the medical connector 100 as compared with a configuration that does not include the above-described rotation control section 3.

That is, when the first connection section 1 tries to rotate in the second circumferential direction B2, this rotational torque is used by the rotation control section 3 for the rotating operation between the first connection section 1 and the second connection section 2. Accordingly, it is difficult for the above-described rotational torque to act on a connecting portion between the second connection section 2 and the second medical device. Therefore, it becomes difficult for the second connection section 2 to rotate in the second circumferential direction B2 relative to the second medical device. In this manner, even if an external force that tries to release the connection state between the second connection section 2 and the second medical device acts on the position of the first connection section 1, this external force can be suppressed from acting on the connecting portion between the second connection section 2 and the second medical device by the rotation control section 3. Therefore, it is possible to prevent the connection state between the medical connector 100 and the second medical device from being unintentionally released. As a result, it is possible to realize a configuration in which the connection state between the medical connector 100 and the second medical device is easily maintained.

Hereinafter, more details of the medical connector 100 of the present embodiment will be described.

The medical connector 100 of the present embodiment includes a first connection member 21 and a second connection member 22. The first connection section 1 of the present embodiment is constituted by the first connection member 21. The second connection section 2 of the present embodiment is constituted by the second connection member 22. Hereinafter, details of the first connection member 21 and the second connection member 22 will be described.

<First Connection Member 21>

The first connection member 21 includes a first housing 31 and a valve body 32 attached to the first housing 31. As described above, the first connection section 1 of the present embodiment is constituted by the first connection member 21. That is, the first connection section 1 of the present embodiment is constituted by the first housing 31 and the valve body 32.

[First Housing 31]

The first housing 31 defines an insertion port for a male connector to be inserted from the outside. The valve body 32 having a slit 33 is located at this insertion port. The insertion port is a hollow portion into which a distal portion of the male connector can be inserted from the outside. The first housing 31 holds the valve body 32 such that the valve body 32 is located in this hollow portion. In other words, the insertion port of the first housing 31 means a hollow portion of a part where the valve body 32 is located in a state in which the valve body 32 is attached to the first housing 31. The hollow portion inside the valve body 32, that is, the hollow portion continuous with the inside of the insertion port is a passage. The first passage 1*a* of the first connection section 1 is constituted by the above-described passage that is continuous with the inside of the insertion port. In other words, one end of the first passage 1*a* is closed by the valve body 32 arranged at the position of the insertion port.

More specifically, the first housing 31 of the present embodiment includes: a cap 34 that defines the insertion port and a part of the passage; and a holder 35 that defines a part of the passage and supports the cap 34.

The cap 34 includes a top face cap 36 and a bottom face cap 37. The insertion port is defined by a part of the top face cap 36 and a part of the bottom face cap 37. The periphery of the valve body 32 is compressed and held by the top face cap 36 and the bottom face cap 37, whereby the position of the valve body 32 in the insertion port is fixed. The valve body 32 will be described below.

The holder 35 supports the top face cap 36 and the bottom face cap 37 that serve as the cap 34. Both the top face cap 36 and the bottom face cap 37 are configured to be supported by the holder 35 in a contact manner in the present embodiment, but a configuration in which the bottom face cap 37 is held by the top face cap 36, and only the top face cap 36 is brought into contact with the holder 35 so as to be supported by the holder 35 may be employed. On the contrary, it may be configured such that the top face cap 36 is held by the bottom face cap 37, and only the bottom face cap 37 is brought into contact with the holder 35 so as to be supported by the holder 35.

As illustrated in FIG. 4, the top face cap 36 includes a substantially cylindrical hollow tubular portion 36*a* and a flange 36*b* provided on one end side of the hollow tubular portion 36*a*. As illustrated in FIG. 4, an upper face 38 formed of an annular plane is provided on the other end side of the hollow tubular portion 36*a*. The upper face 38 includes a substantially circular edge 39 that defines one end of the above-described insertion port. A male screw portion 40 is formed on an outer wall of the hollow tubular portion 36*a* so as to be screwable with a lock-type male connector or male connector portion conforming to ISO 80369-7 in 2016. The flange 36*b* is a portion that is molded integrally with the hollow tubular portion 36*a*, and the top face cap 36 is held by the holder 35 as the flange 36*b* is engaged with the holder 35 to be described below.

A locking projection 41 is provided on an inner wall of the hollow tubular portion 36*a*. This locking projection 41 projects in an insertion direction C of the male connector (a direction in which the male connector is inserted into the first connection section 1, the same direction as one direction of the axial direction A in the present embodiment), and sandwiches the valve body 32 together with a locking projection 42 of the bottom face cap 37, which will be described, to be compressed and held.

As illustrated in FIG. 4, the bottom face cap 37 includes a substantially cylindrical hollow tubular portion 37*a* and a flange 37*b* that is provided on one end side of the hollow tubular portion 37*a* similarly to the top face cap 36. The locking projection 42 is provided on the other end side of the hollow tubular portion 37*a*. The locking projection 42 projects in a removal direction D of the male connector, which is a direction opposite to the insertion direction C of the male connector, and sandwiches the valve body 32 together with the locking projection 41 of the top face cap 36 to be compressed and held.

The bottom face cap 37 is attached to the top face cap 36 by being joined to an inner surface of the hollow tubular portion 36*a* of the top face cap 36 and/or a lower face (the lower face in FIG. 4) of the flange 36*b* by ultrasonic welding or the like. Further, the bottom face cap 37 is also attached to the holder 35 by joining the flange 37*b* of the bottom face cap 37 to the holder 35, which will be described below, by ultrasonic welding or the like.

As illustrated in FIG. 4, the holder 35 supports the top face cap 36 and the bottom face cap 37, and defines a passage inside thereof.

More specifically, the holder 35 includes a substantially cylindrical inner tubular portion 35*a*, an annular support portion 35*b*, and a substantially cylindrical outer tubular portion 35*c*. The inner tubular portion 35*a* defines a passage. The annular support portion 35*b* projects radially outward from an outer wall of the inner tubular portion 35*a* on one end side (the upper side in FIG. 4) of the inner tubular portion 35*a* in the axial direction (the same direction as the axial direction A in the present embodiment), and supports the top face cap 36 and the bottom face cap 37 described above. The outer tubular portion 35*c* projects from the support portion 35*b* toward the other end side (the lower side in FIG. 4) of the inner tubular portion 35*a* in the axial direction, and is located outside the inner tubular portion 35*a* in the radial direction.

As illustrated in FIG. 4, the inner tubular portion 35*a* is fitted with a connecting inner tubular portion 52*a* of the second housing 51 of the second connection member 22 to be described below. Specifically, the connecting inner tubular portion 52*a* of the second housing 51 of the second connection member 22, which will be described below, is fitted in the inner tubular portion 35*a*. More specifically, when one end side in the axial direction of the inner tubular portion 35*a* that is continuous with the support portion 35*b* is defined as a proximal side and the opposite side thereof is defined as a distal side, the connecting inner tubular portion 52*a* of the second housing 51 of the second connection member 22 is inserted from the distal side of the inner tubular portion 35*a* and is fitted in the inner tubular portion 35*a*.

Figure 5:
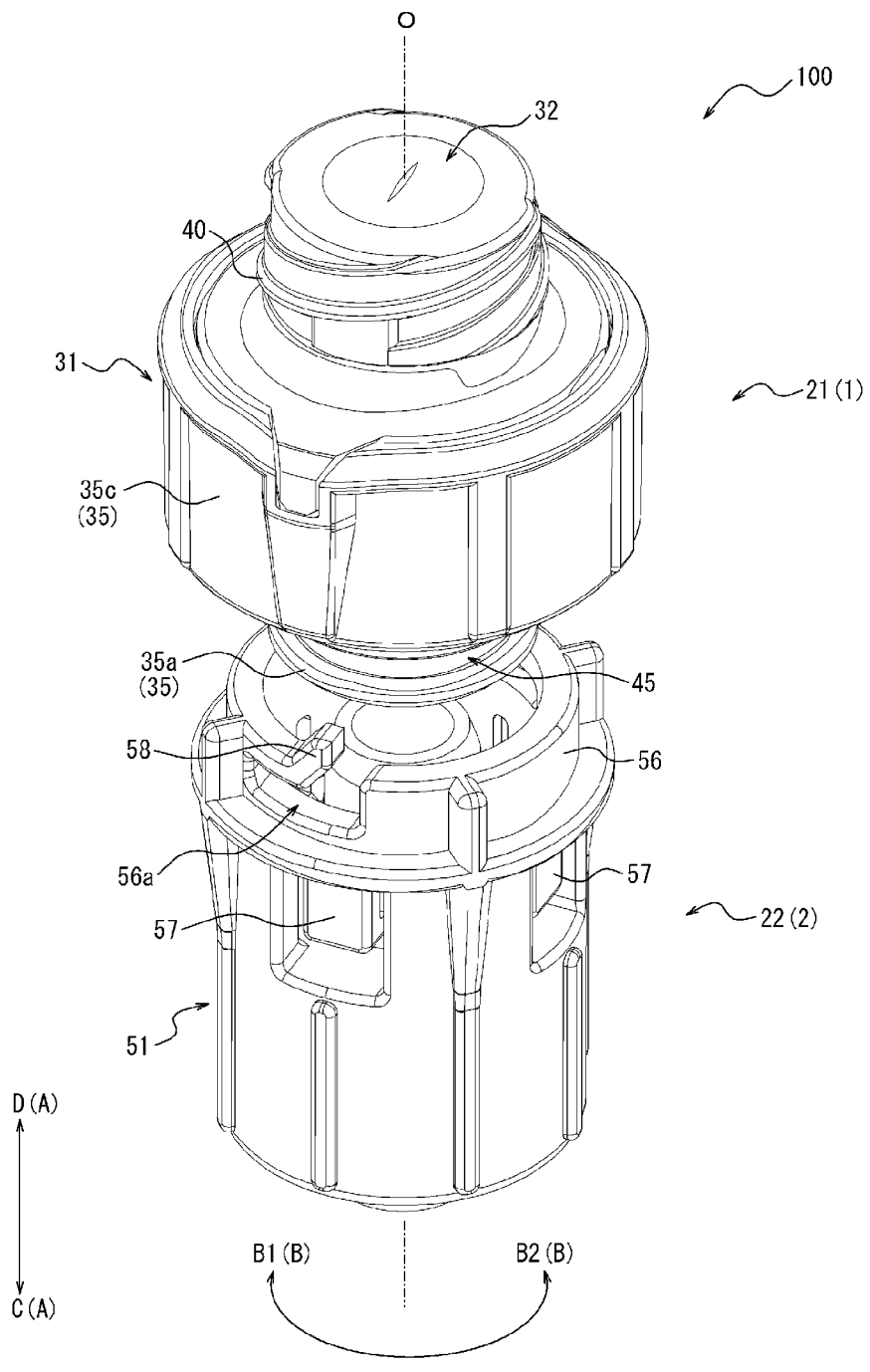
FIG. 5 is an exploded perspective view of the medical connector illustrated in FIG. 1 as viewed from the top surface.
Figure 6:
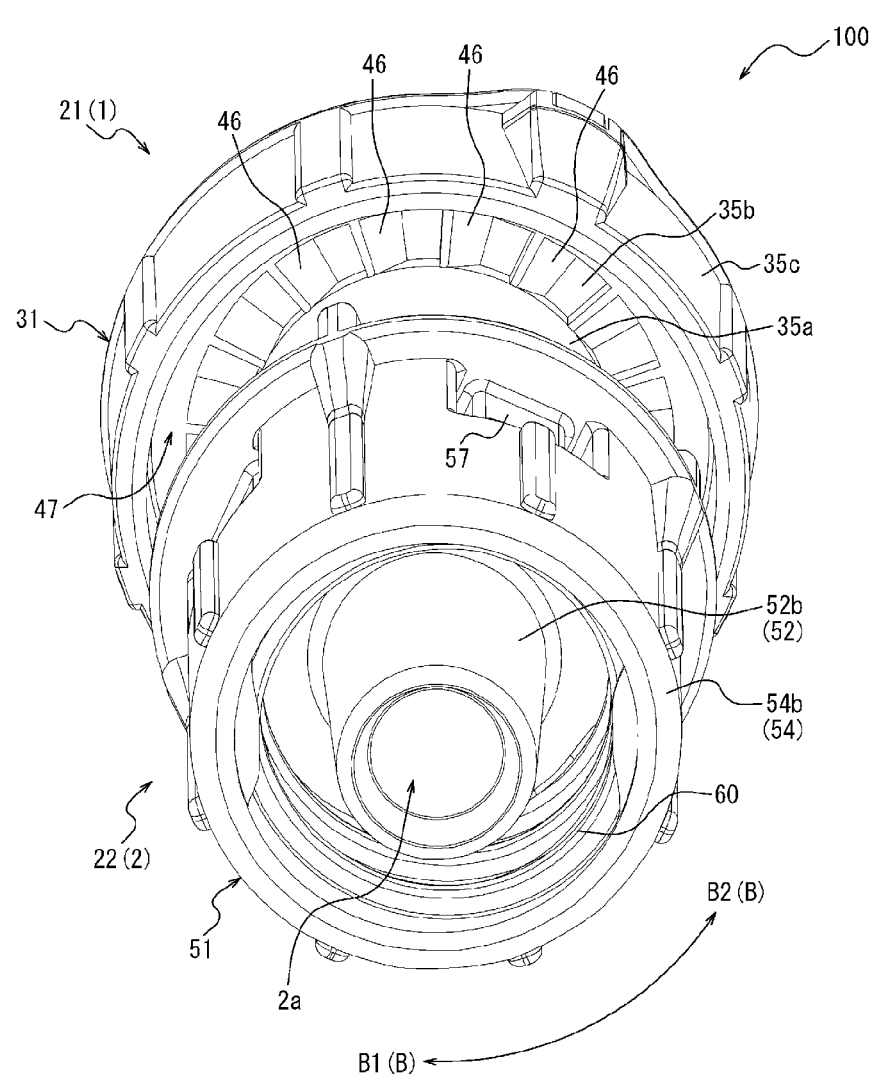
FIG. 6 is an exploded perspective view of the medical connector illustrated in FIG. 1 as viewed from a bottom surface.
Figure 7:
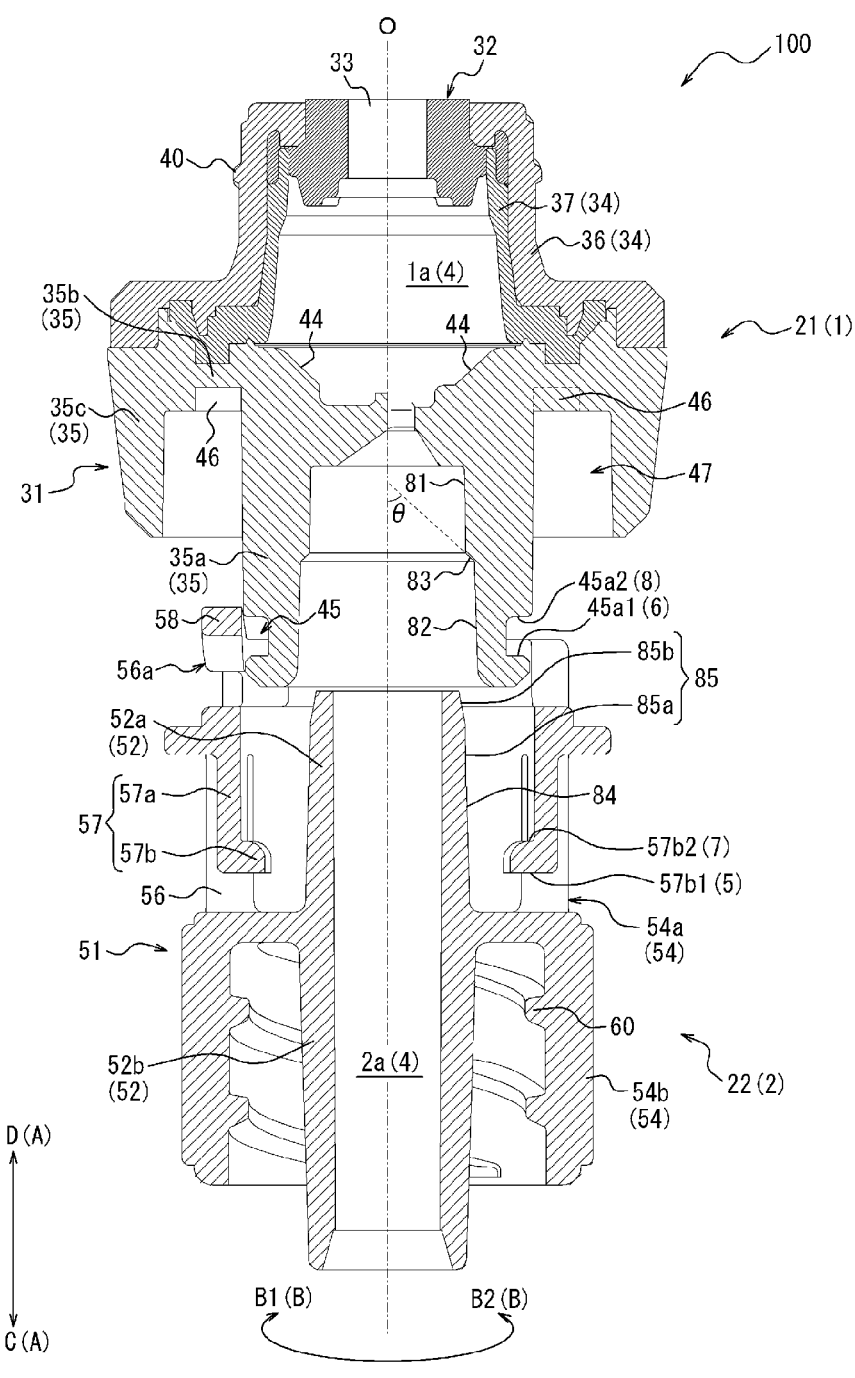
FIG. 7 is a cross-sectional view illustrating the same cross section as FIG. 4 in a state in which the medical connector illustrated in FIG. 1 is disassembled into a first connection member and a second connection member.

FIG. 5 is an exploded perspective view of the medical connector 100 as viewed from the top surface. FIG. 6 is an exploded perspective view of the medical connector 100 as viewed from a bottom surface. FIG. 7 is a cross-sectional view illustrating the same cross section as FIG. 4 in a state in which the medical connector 100 is disassembled into the first connection member 21 and the second connection member 22, in other words, in a state before the first connection member 21 and the second connection member 22 are connected.

As illustrated in FIG. 7, an inner peripheral face of the inner tubular portion 35*a* includes: a proximal inner peripheral face 81 located on the proximal side; a distal inner peripheral face 82 located on the distal side and extending to a distal end; and an intermediate inner peripheral face 83 located between the proximal inner peripheral face 81 and the distal inner peripheral face 82 in the axial direction of the inner tubular portion 35*a*.

Each of the proximal inner peripheral face 81, the distal inner peripheral face 82, and the intermediate inner peripheral face 83 is a tapered face that increases in diameter from the proximal side (the upper side in FIG. 7) to the distal side (the lower side in FIG. 7). However, with regard to a taper angle with respect to an axis of the inner tubular portion 35*a*, a taper angle of the intermediate inner peripheral face 83 is larger than taper angles of the proximal inner peripheral face 81 and the distal inner peripheral face 82. Although the taper angle of the intermediate inner peripheral face 83 is illustrated as "θ" in FIG. 7, the taper angle of each of the proximal inner peripheral face 81 and the distal inner peripheral face 82 means an angle at a similar position.

As described above, each of the proximal inner peripheral face 81 and the distal inner peripheral face 82 of the present embodiment is constituted by the tapered surface, but the present invention is not limited to this configuration, and may have an inner peripheral face having a uniform inner diameter in the axial direction of the inner tubular portion 35*a*. Further, the taper angle of the proximal inner peripheral face 81 and the taper angle of the distal inner peripheral face 82 are substantially equal in the present embodiment, but may be different angles.

As illustrated in FIG. 4, an outer peripheral face of the connecting inner tubular portion 52*a* of the second housing 51 of the second connection member 22 is fitted in the inner tubular portion 35*a*. The outer peripheral face of the connecting inner tubular portion 52*a* of the second housing 51 of the second connection member 22 is in close contact with the proximal inner peripheral face 81 of the inner tubular portion 35*a* (see FIG. 7). As illustrated in FIG. 7, a distal outer peripheral face 85 that is in close contact with the above-described proximal inner peripheral face 81 is formed even in the outer peripheral face of the connecting inner tubular portion 52*a* of the second housing 51 of the second connection member 22, and details of the distal outer peripheral face 85 will be described below (see FIG. 7).

As illustrated in FIGS. 4 and 7, an insertion restricting portion 44 is provided on an inner wall of the inner tubular portion 35*a*. The insertion restricting portion 44 restricts further insertion of the male connector in the insertion direction C as a distal end of the male connector inserted from the insertion port of the cap 34 abuts thereon. As illustrated in FIG. 7, the proximal inner peripheral face 81, the intermediate inner peripheral face 83, and the distal inner peripheral face 82 are arranged in the axial direction of the inner tubular portion 35*a* on the side of the insertion direction C of the male connector (the lower side in FIG. 7) that is on the distal side of the insertion restricting portion 44.

As illustrated in FIG. 7 and the like, an annular groove 45 extending in a circumferential direction (the same direction as the circumferential direction B in the present embodiment) is formed on the outer wall of the inner tubular portion 35*a*. More specifically, the annular groove 45 of the present embodiment is formed in a portion of the outer wall in a region where the distal inner peripheral face 82 (see FIG. 7) of the inner tubular portion 35*a* is formed. As illustrated in FIG. 4, a claw portion 57 of the second housing 51 of the second connection member 22 is fitted into the annular groove 45. Details of the claw portion 57 will be described below.

As illustrated in FIG. 6, a plurality of convex portions 46 are formed on a face (hereinafter, simply referred to as a "lower face of the support portion 35*b*") of the annular support portion 35*b* opposite to a face supporting the cap 34 (see FIG. 4). More specifically, a plurality of convex portions 46 arranged at a predetermined pitch in the circumferential direction (the same direction as the circumferential direction B in the present embodiment) are formed on the lower face of the support portion 35*b*. Although details will be described below, the plurality of convex portions 46 constitute a part of the ratchet mechanism of the rotation control section 3 (see FIGS. 8 to 11 and 14).

As illustrated in FIGS. 4 to 7, the outer tubular portion 35*c* is located outside the inner tubular portion 35*a* in the radial direction. Further, an annular gap 47 is formed between the inner tubular portion 35*a* and the outer tubular portion 35*c*. A part of the second housing 51 of the second connection member 22, which will be described below, enters the gap 47. A deformation portion 58, which constitutes the ratchet mechanism together with the plurality of convex portions 46 described above, is provided in a part of the second housing 51 of the second connection member 22 although details will be described below (see FIGS. 8 to 11, 14, and 15).

The holder 35, the top face cap 36, and the bottom face cap 37 that constitute the first housing 31 of the present embodiment are made of polypropylene, but are not limited to this material. Examples of materials for the holder 35 and the top face cap 36 and the bottom face cap 37, serving as the cap 34, which form the first housing 31, include various resin materials; for example polyolefin such as polyethylene, polypropylene, and an ethylene-propylene copolymer; an ethylene-vinyl acetate copolymer (EVA); polyvinyl chloride; polyvinylidene chloride; polystyrene; polyamide; polyimide; polyamide-imide; polycarbonate; poly(4-methylpentene-1); ionomer; an acrylic resin; polymethyl methacrylate; an acrylonitrile-butadiene-styrene copolymer (ABS resin); an acrylonitrile-styrene copolymer (AS resin); a butadiene-styrene copolymer; polyester such as polyethylene terephthalate (PET), polybutylene terephthalate (PBT), and polycyclohexane terephthalate (PCT); polyether; polyether ketone (PEK); polyether ether ketone (PEEK); polyether imide; polyacetal (POM); polyphenylene oxide; modified polyphenylene oxide; polysulfone; polyether sulfone; polyphenylene sulfide; polyarylate; aromatic polyester (a liquid crystal polymer); and polytetrafluoroethylene, polyvinylidene fluoride and other fluororesins. Further, a blend or a polymer alloy containing one or more kinds of the above materials may also be used. Alternatively, various glass materials, ceramic materials, or metal materials may be used.

The first housing 31 of the first connection member 21 of the present embodiment is constituted by three members of the holder 35, the top face cap 36, and the bottom face cap 37, but is not limited to this configuration, and may be constituted by two members, for example by integrally molding the holder 35 and the bottom face cap 37. Further, the first housing may be constituted by a single member or four or more members.

[Valve Body 32]

As illustrated in FIG. 4, the valve body 32 is provided with a slit 33 such that the valve body 32 can be elastically deformed to be open and closed when the male connector is attached to and detached from the medical connector 100. Further, the valve body 32 is arranged so as to close the insertion port formed by the top face cap 36 and the bottom face cap 37 serving as the cap 34. Specifically, the position of the valve body 32 is fixed by being held by a holding portion formed by the top face cap 36 and the bottom face cap 37.

The valve body 32 is molded and formed to be elastically deformable. Examples of the material of the valve body 32 include various rubber materials such as natural rubber, isoprene rubber, butadiene rubber, styrene-butadiene rubber, nitrile rubber, chloroprene rubber, butyl rubber, acrylic rubber, ethylene-propylene rubber, hydrin rubber, urethane rubber, silicone rubber, and fluoro rubber; and various thermoplastic elastomers such as a styrene-based thermoplastic elastomer, a polyolefin-based thermoplastic elastomer, a polyvinyl chloride-based thermoplastic elastomer, a polyurethane-based thermoplastic elastomer, a polyester-based thermoplastic elastomer, a polyamide-based thermoplastic elastomer, a polybutadiene-based thermoplastic elastomer, a transpolyisoprene-based thermoplastic elastomer, a fluoro rubber-based thermoplastic elastomer, and a chlorinated polyethylene-based thermoplastic elastomer, and a configuration obtained by mixing one or two or more kinds of these materials may be used.

Further, the hardness of the valve body 32 is preferably 20 to 60° (A hardness). Accordingly, it is possible to ensure a moderate elastic force in the valve body 32, and thus, elastic deformation (described below) can be generated in the valve body 32.

<Second Connection Member 22>

As illustrated in FIGS. 4 to 7, the second connection member 22 includes the second housing 51. As described above, the second connection section 2 of the present embodiment is constituted by the second connection member 22. That is, the second connection section 2 of the present embodiment is constituted by the second housing 51.

[Second Housing 51]

As illustrated in FIGS. 4 to 7, the second housing 51 includes a substantially cylindrical inner tubular portion 52, an annular flange 53, and a substantially cylindrical outer tubular portion 54. The inner tubular portion 52 defines a passage as the second passage 2a. The annular flange 53 projects radially outward from an outer wall of the inner tubular portion 52. The outer tubular portion 54 projects from the annular flange 53 in the axial direction of the inner tubular portion 52 (the same direction as the axial direction A in the present embodiment).

The inner tubular portion 52 includes the connecting inner tubular portion 52a and a distal inner tubular portion 52b. The connecting inner tubular portion 52a projects from the annular flange 53 to one end side (the upper side in FIG. 4) of the inner tubular portion 52 in the axial direction, and is inserted into the inner tubular portion 35a of the first connection member 21 described above. The distal inner tubular portion 52b projects from the annular flange 53 to the other end side of the inner tubular portion 52 (the lower side in FIG. 4) in the axial direction.

As illustrated in FIG. 7, an outer peripheral face of the connecting inner tubular portion 52a of the inner tubular portion 52 includes: a proximal outer peripheral face 84 continuous with the annular flange 53; and a distal outer peripheral face 85 that is located on the distal side and extends to the distal end.

Each of the proximal outer peripheral face 84 and the distal outer peripheral face 85 is a tapered face whose diameter decreases from the proximal side to the distal side (from the lower side to the upper side in the connecting inner tubular portion 52a illustrated in FIG. 7).

As described above, each of the proximal outer peripheral face 84 and the distal outer peripheral face 85 of the present embodiment is constituted by the tapered surface, but the present invention is not limited to this configuration, and may have an inner peripheral face having a uniform inner diameter in the axial direction of the connecting inner tubular portion 52a. Each of the proximal outer peripheral face 84 and the distal outer peripheral face 85 may be configured to have a uniform taper angle regardless of the position in the axial direction. In this case, taper angles of the proximal outer peripheral face 84 and the distal outer peripheral face 85 may be substantially equal or different. The taper angle of the proximal outer peripheral face 84 and a taper angle of a distal base portion face 85a, which will be described below, of the distal outer peripheral face 85 are different in the present embodiment, but may be approximately equal.

As illustrated in FIG. 7, the distal outer peripheral face 85 of the present embodiment is configured by two tapered surfaces having different taper angles. Specifically, the distal outer peripheral face 85 of the present embodiment is constituted by the distal base portion face 85a continuous with the proximal outer peripheral face 84 and a distal portion face 85*b* that has a larger taper angle than the distal base portion face 85*a* and extends to the distal end. The distal outer peripheral face 85 may be constituted by one cylindrical face or tapered surface, but is preferably constituted by a plurality of outer peripheral faces having different taper angles as in the present embodiment. Then, the connecting inner tubular portion 52*a* can be smoothly fitted with the inner tubular portion 35*a* of the first housing 31 of the first connection member 21 when the second connection member 22 is connected to the first connection member 21.

As illustrated in FIG. 4, an inner peripheral face of the inner tubular portion 35*a* of the first housing 31 of the first connection member 21 externally fitted to the connecting inner tubular portion 52*a* is in close contact with the distal outer peripheral face 85 of the connecting inner tubular portion 52*a* (see FIG. 7). More specifically, the distal outer peripheral face 85 of the connecting inner tubular portion 52*a* (see FIG. 7) is in close contact with the proximal inner peripheral face 81 of the inner tubular portion 35*a* of the first housing 31 of the first connection member 21 (see FIG. 7).

In this manner, the connecting inner tubular portion 52*a* of the second housing 51 is inserted into the inner tubular portion 35*a* of the first housing 31, thereby forming an insertion region T1 in the axial direction A where the inner tubular portion 35*a* and the connecting inner tubular portion 52*a* overlap in the radial direction. As illustrated in FIG. 4, an abutment region T2 where the inner peripheral face of the inner tubular portion 35*a* is in close contact with the outer peripheral face of the connecting inner tubular portion 52*a* is only a part of the above-described insertion region T1. Then, a sliding resistance when the first connection member 21 and the second connection member 22 relatively rotate can be reduced as compared with the configuration in which the abutment region T2 is the entire insertion region T1.

In the present embodiment, the taper angle of the distal base portion face 85*a* with respect to the axial direction A is smaller than the taper angle of the intermediate inner peripheral face 83 with respect to the axial direction A (see "θ" in FIG. 7). Then, it is easy to realize the configuration in which the distal base portion face 85*a* does not abut on the intermediate inner peripheral face 83 but abuts on the proximal inner peripheral face 81. Further, the taper angle of the distal base portion face 85*a* with respect to the axial direction A is larger than the taper angle of the proximal inner peripheral face 81 with respect to the axial direction A. Then, it is possible to prevent the connecting inner tubular portion 52*a* from being excessively inserted into the inner tubular portion 35*a*. Accordingly, the abutment region T2 in the axial direction A between the distal base portion face 85*a* and the proximal inner peripheral face 81 can be reduced. In this manner, the taper angle of the distal base portion face 85*a* with respect to the axial direction A is preferably smaller than the taper angle of the intermediate inner peripheral face 83 with respect to the axial direction A (see "θ" in FIG. 7) and larger than the taper angle of the proximal inner peripheral face 81 with respect to the axial direction A.

The abutment region T2 of the present embodiment is formed over the entire region in the circumferential direction (the same direction as the circumferential direction B in the present embodiment) of the inner tubular portion 35*a* and the connecting inner tubular portion 52*a*. That is, the proximal inner peripheral face 81 (see FIG. 7) of the inner peripheral face of the inner tubular portion 35*a* abuts on the distal outer peripheral face 85 (see FIG. 7) of the outer peripheral face of the connecting inner tubular portion 52*a* in the entire circumferential region. Accordingly, the first passage 1*a* of the first connection section 1 defined by the first connection member 21 and the second passage 2*a* of the second connection section 2 defined by the second connection member 22 are connected in a liquid-tight manner. In this manner, a sealing property of a connection point may be ensured by causing the connecting inner tubular portion 52*a* of the second connection member 22 and the inner tubular portion 35*a* of the first connection member 21 to abut on each other. Further, the sealing property may be ensured by interposing another member, such as an O-ring, between the outer wall of the connecting inner tubular portion 52*a* and the inner wall of the inner tubular portion 35*a*.

The distal inner tubular portion 52*b* of the inner tubular portion 52 is, for example, a male luer portion conforming to ISO 80369-7 in 2016.

As illustrated in FIG. 4, the outer tubular portion 54 includes a substantially cylindrical connecting outer tubular portion 54*a* and a substantially cylindrical distal outer tubular portion 54*b*. The connecting outer tubular portion 54*a* projects from an outer edge of the annular flange 53 to one end side (the upper side in FIG. 4) of the inner tubular portion 52 in the axial direction, and is located radially around the connecting inner tubular portion 52*a* of the inner tubular portion 52. The distal outer tubular portion 54*b* projects from the outer edge of the annular flange 53 to the other end side (the lower side in FIG. 4) of the inner tubular portion 52 in the axial direction, and is located radially around the distal inner tubular portion 52*b* of the inner tubular portion 52.

As illustrated in FIG. 4, the connecting outer tubular portion 54*a* of the outer tubular portion 54 includes a peripheral wall portion 56 and the claw portion 57. The claw portion 57 is only partially continuous with the peripheral wall portion 56, and can be elastically deformed in the radial direction of the peripheral wall portion 56 at positions other than the continuous position.

In the claw portion 57 of the present embodiment, only one side (the upper side in FIG. 4) of the peripheral wall portion 56 in the axial direction (the same direction as the axial direction A in the present embodiment) is continuous with the peripheral wall portion 56. On the other hand, the claw portion 57 of the present embodiment is not continuous with the peripheral wall portion 56 on the other side of the peripheral wall portion 56 in the axial direction and on both sides of the peripheral wall portion 56 in the circumferential direction. Therefore, the claw portion 57 of the present embodiment can be elastically deformed in the radial direction of the peripheral wall portion 56 to swing with the position continuous with the peripheral wall portion 56 on one side of the peripheral wall portion 56 in the axial direction as a fulcrum. As illustrated in FIG. 1 and the like, a plurality of (four in the present embodiment) claw portion 57 of the present embodiment are provided at different positions in the circumferential direction of the peripheral wall portion 56 (the same direction as the circumferential direction B in the present embodiment).

More specifically, the claw portion 57 of the present embodiment includes a deformation portion 57*a* and a locking projection 57*b*. The deformation portion 57*a* can be elastically deformed in the radial direction of the peripheral wall portion 56. The locking projection 57*b* projects radially inward of the peripheral wall portion 56 from a distal portion of the deformation portion 57*a*.

As described above, the annular groove 45 (see FIG. 4 and the like) extending in the circumferential direction is formed in the outer wall of the inner tubular portion 35*a* of the first housing 31 of the first connection member 21. The claw portion 57 of the present embodiment is located radially outside the inner tubular portion 35a of the first housing 31 of the first connection member 21. The first connection member 21 and the second connection member 22 can be connected by fitting the locking projection 57b of the claw portion 57 into the annular groove 45. The claw portion 57 is elastically deformable in the radial direction as described above. With such a configuration, it is possible to suppress an increase in sliding resistance when the inner tubular portion 35a and the connecting inner tubular portion 52a relatively rotate.

As illustrated in FIG. 5, the connecting outer tubular portion 54a of the outer tubular portion 54 further includes the deformation portion 58. The deformation portion 58 is inserted into the annular gap 47 between the inner tubular portion 35a and the outer tubular portion 35c of the first connection member 21 (see FIG. 6 and the like) and is engaged with the plurality of convex portions 46 (see FIG. 6) formed on the lower face of the support portion 35b of the first connection member 21.

More specifically, the deformation portion 58 of the present embodiment is constituted by a projecting portion that projects from the above-described peripheral wall portion 56. As illustrated in FIG. 5, a notch-shaped concave portion 56a is formed on an end face in the axial direction (the same direction as the axial direction A in the present embodiment) in the peripheral wall portion 56 of the present embodiment. The projecting portion serving as the deformation portion 58 of the present embodiment projects from a position of an edge of the concave portion 56a on the end face of the peripheral wall portion 56 toward the concave portion 56a in the circumferential direction of the peripheral wall portion 56 (the same direction as the circumferential direction B in the present embodiment). Further, the projecting portion serving as the deformation portion 58 of the present embodiment is continuous with the edge of the concave portion 56a, and is integrally molded with the peripheral wall portion 56. The projecting portion serving as the deformation portion 58 can be elastically deformed in the axial direction of the peripheral wall portion 56 to swing with the edge of the concave portion 56a as a fulcrum. In an end face in the axial direction of the peripheral wall portion 56 of the present embodiment, two notched concave portions 56a are provided at different positions in the circumferential direction. One deformation portion 58 is provided at the position of each of the concave portions 56a. The two concave portions 56a may be formed at positions opposing each other the radial direction of the peripheral wall portion 56, or may be formed at positions not opposing each other in the radial direction. The number and circumferential positions of the concave portions 56a and the deformation portions 58 are not limited to the number and the circumferential positions illustrated in the present embodiment, and can be appropriately designed. More details of the projecting portion serving as the deformation portion 58 of the present embodiment will be described below (see FIGS. 8 to 11, 14, and 15).

As illustrated in FIG. 4 and the like, a female screw portion 60 is formed on an inner wall of the distal outer tubular portion 54b of the outer tubular portion 54. The female screw portion 60 can be screwed with a lock-type female connector or female connector portion conforming to ISO 80369-7 in 2016.

Although the second housing 51 of the present embodiment is formed using polycarbonate, a material of the second housing 51 is not limited to this material. As the material of the second housing 51, for example, the materials exemplified as the material of the first housing 31 of the first connection member 21 described above can be used.

The second housing 51 of the second connection member 22 of the present embodiment is constituted by one member, but is not limited to this configuration, and may be constituted by two or more members.

[Ratchet Mechanism Formed of First Housing 31 and Second Housing 51]

The first housing 31 of the first connection member 21 and the second housing 51 of the second connection member 22 form the ratchet mechanism. The rotation control section 3 of the present embodiment includes the ratchet mechanism, and thus, can execute the above-described rotation control. Hereinafter, details of the ratchet mechanism of the present embodiment will be described.

Figure 8:
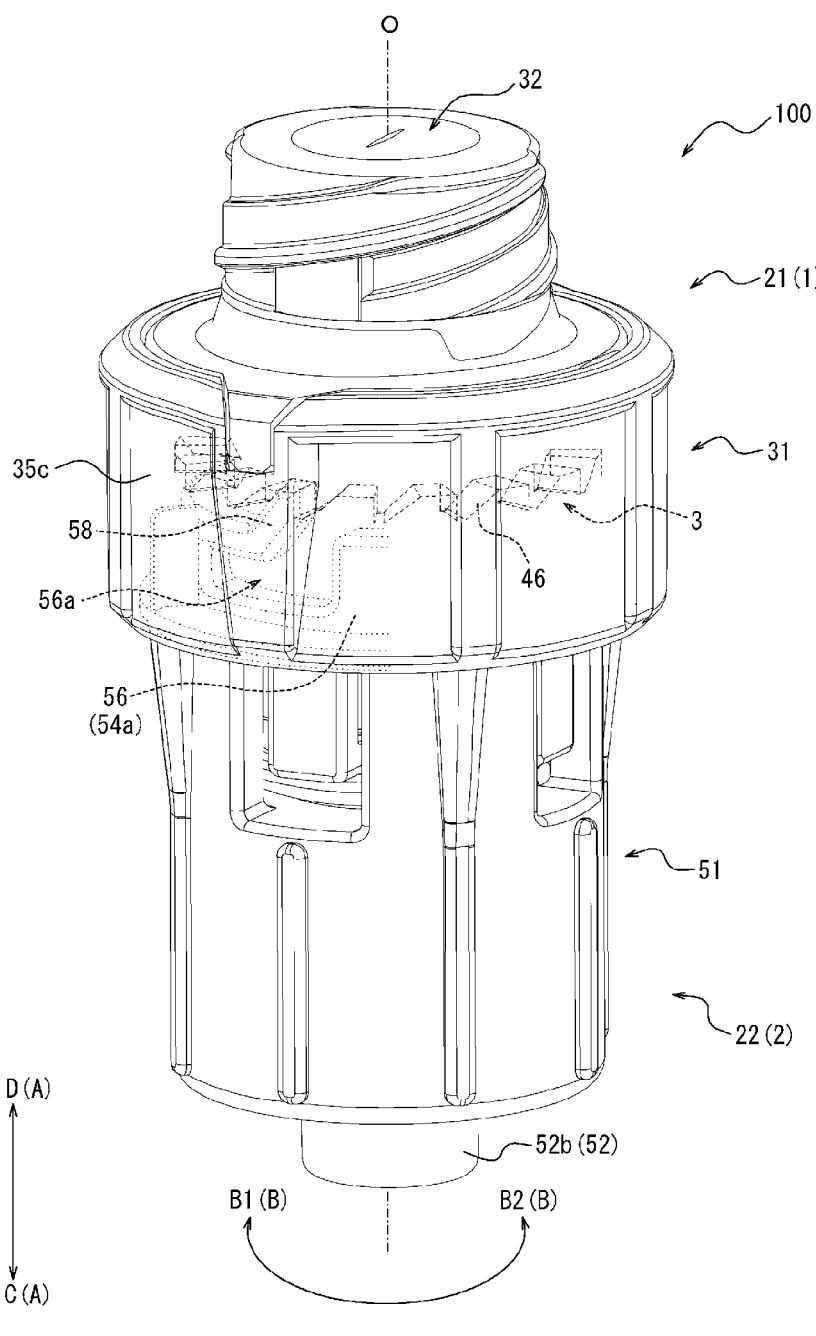
FIG. 8 is a view illustrating a ratchet mechanism in a rotation control section of the medical connector illustrated in FIG. 1.

FIG. 8 is a view illustrating the ratchet mechanism formed of the first housing 31 and the second housing 51. As described above, the plurality of convex portions 46 (see FIG. 6 and the like) are provided on the lower face of the support portion 35b of the first housing 31 (see FIG. 4, FIG. 6, and the like) so as to repeat irregularities along the circumferential direction of the outer tubular portion 35c (the same direction as the circumferential direction B in the present embodiment). More specifically, the plurality of convex portions 46 are arranged over the entire region in the circumferential direction B at substantially equal pitches along the circumferential direction B.

On the other hand, the projecting portion serving as the deformation portion 58 is provided on the end face of the peripheral wall portion 56 of the connecting outer tubular portion 54a of the second housing 51. As illustrated in FIG. 8, the deformation portion 58 is configured to fit into a recess between the convex portions 46 adjacent in the circumferential direction B in a state in which the first connection member 21 and the second connection member 22 are connected. In other words, at least a part of the deformation portion 58 and a part of the convex portion 46 are arranged at positions overlapping in the circumferential direction B in the state in which the first connection member 21 and the second connection member 22 are connected.

Figure 9:
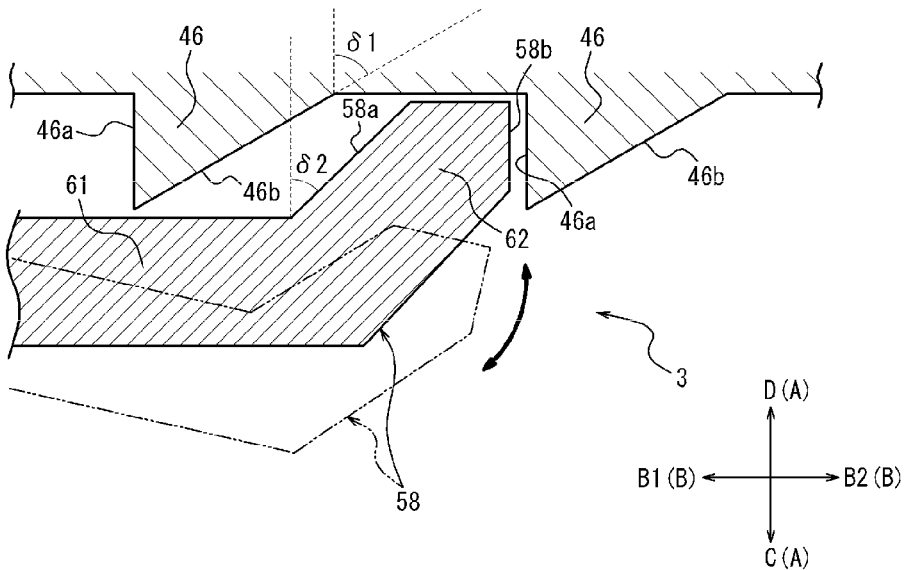
FIG. 9 is a view illustrating an outline of the ratchet mechanism illustrated in FIG. 8.

FIG. 9 is a view illustrating an outline of the ratchet mechanism including the plurality of convex portions 46 of the first housing 31 and the deformation portion 58 of the second housing 51. As illustrated in FIG. 9, angles of side faces on both sides in the circumferential direction B of each of the convex portions 46 with respect to the axial direction A are different. Specifically, the angle of a first side face 46a located on the side of the first circumferential direction B1, which is one side of the convex portion 46 in the circumferential direction B, with respect to the axial direction A is smaller than the angle (see "δ1" in FIG. 9) of a second side face 46b located on the side of the second circumferential direction B2, which is the other side of the convex portion 46 in the circumferential direction B, with respect to the axial direction A. In other words, the first side face 46a on the side of the first circumferential direction B1 of the convex portion 46 extends along the axial direction A more than the second side face 46b on the side of the second circumferential direction B2 of the convex portion 46. In the example illustrated in FIG. 9, the angle of the first side face 46a on the side of the first circumferential direction B1 of the convex portion 46 with respect to the axial direction A is 0 degree, and the first side face 46a extends substantially parallel to the axial direction A.

The distal side of the projecting portion serving as the deformation portion 58 is configured to be capable of swinging (see a two-dot chain line and a thick arrow in FIG.

9) by being elastically deformed in the axial direction A. Specifically, the projecting portion serving as the deformation portion 58 includes a first abutment face 58*a* located on the side of the first circumferential direction B1 and a second abutment face 58*b* located on the side of the second circumferential direction B2. As illustrated in FIG. 9, an angle of the second abutment face 58*b* with respect to the axial direction A is smaller than an angle of the first abutment face 58*a* with respect to the axial direction A (see "δ2" in FIG. 9). In other words, the second abutment face 58*b* extends along the axial direction A more than the first abutment face 58*a*. In the example illustrated in FIG. 9, the angle of the second abutment face 58*b* with respect to the axial direction A is 0 degree, and the second abutment face 58*b* extends substantially parallel to the axial direction A.

In the present embodiment, the angles of the first side face 46*a* and the second side face 46*b* of the convex portion 46 and the angles of the first abutment face 58*a* and the second abutment face 58*b* of the deformation portion 58 with respect to the axial direction A are set to have the above-described inclination relation, thereby realizing the ratchet mechanism of the rotation control section 3.

Specifically, when the projecting portion serving as the deformation portion 58 rotates in the first circumferential direction B1 relative to the convex portion 46, the second side face 46*b* of the convex portion 46 abuts and slides on the first abutment face 58*a* of the deformation portion 58. Accordingly, a distal portion 62 near the first abutment face 58*a* of the deformation portion 58 is pressed in the insertion direction C by the second side face 46*b*, and the distal portion 62 of the deformation portion 58 is elastically deformed in the insertion direction C (see a two-dot chain line in FIG. 9). Accordingly, the deformation portion 58 can advance over the convex portion 46.

In other words, according to this ratchet mechanism, the relative rotation of the second connection member 22 constituting the second connection section 2 (see FIG. 8) in the first circumferential direction B1 relative to the first connection member 21 constituting the first connection section 1 (see FIG. 8) is allowed.

Conversely, when the projecting portion serving as the deformation portion 58 rotates in the second circumferential direction B2 relative to the convex portion 46, the first side face 46*a* of the convex portion 46 comes into contact with the second abutment face 58*b* of the deformation portion 58, but the both do not slide. Rather, the first side face 46*a* of the convex portion 46 of the present embodiment pushes up the projecting portion serving as the deformation portion 58 in the removal direction D, which is the opposite direction of the insertion direction C, via the second abutment face 58*b* so as to be pushed into the recess between the convex portions 46. In this manner, the first side face 46*a* of the convex portion 46 does not press the distal portion 62 near the second abutment face 58*b* of the deformation portion 58 in the insertion direction C, and thus, the distal portion 62 of the deformation portion 58 is not elastically deformed in the insertion direction C. Therefore, it is difficult for the deformation portion 58 to advance over the convex portion 46.

In other words, according to this ratchet mechanism, the relative rotation of the second connection member 22 constituting the second connection section 2 (see FIG. 8) in the second circumferential direction B2 relative to the first connection member 21 constituting the first connection section 1 (see FIG. 8) is restricted.

As illustrated in FIG. 9, the projecting portion serving as the deformation portion 58 of the present embodiment includes a main body portion 61 and the distal portion 62.

Figure 10:
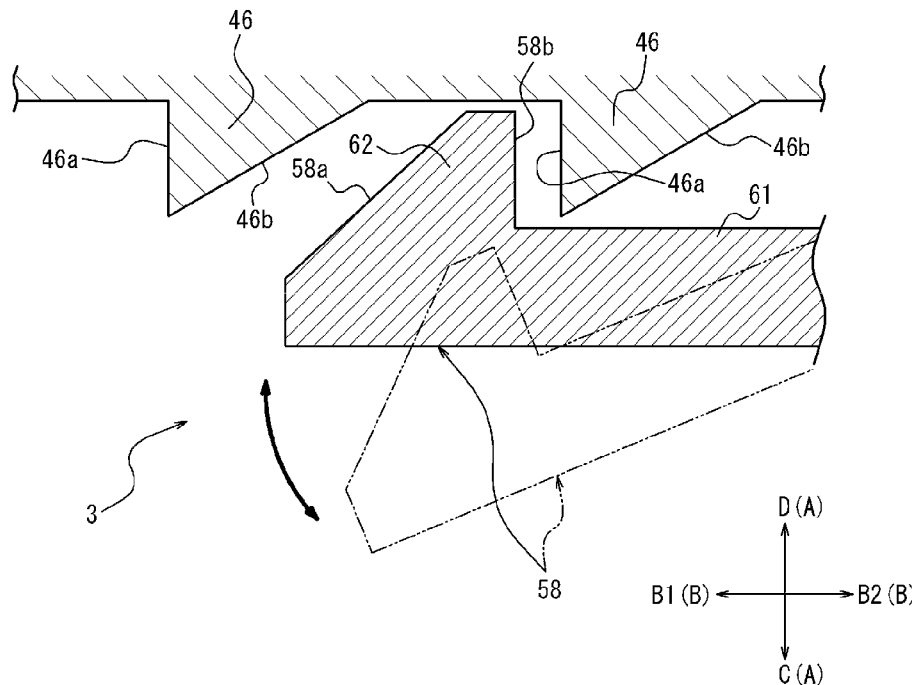
FIG. 10 is a view illustrating a modification of the ratchet mechanism illustrated in FIG. 8.

The main body portion 61 extends in the circumferential direction B, and the distal portion 62, which is elastically deformable in the axial direction A, is provided to project from the main body portion 61 in the removal direction D opposite to the insertion direction C on the distal side of the main body portion 61. The first abutment face 58*a* is formed on a face of the distal portion 62 on the side where the main body portion 61 is located in the circumferential direction B (the side of the first circumferential direction B1 in FIG. 9). The second abutment face 58*b* is formed on a face of the distal portion 62 on the side where the main body portion 61 is not located in the circumferential direction B (the side of the second circumferential direction B2 in FIG. 9). However, the shape of the deformation portion 58 used in the ratchet mechanism is not limited to the shape of the present embodiment, and may be another shape. FIG. 10 is a view illustrating a modification of the deformation portion 58. A projecting portion serving as the deformation portion 58 illustrated in FIG. 10 includes the main body portion 61 and the distal portion 62. However, the first abutment face 58*a* of the deformation portion 58 illustrated in FIG. 10 is formed on a face of the distal portion 62 on the side where the main body portion 61 is not located in the circumferential direction B (the side of the first circumferential direction B1 in FIG. 10). The second abutment face 58*b* of the deformation portion 58 illustrated in FIG. 10 is formed on a face of the distal portion 62 on the side where the main body 61 is located in the circumferential direction B (the side of the second circumferential direction B2 in FIG. 10). With the deformation portion 58 as illustrated in FIG. 10, the durability of the deformation portion 58 can be enhanced as compared with the configuration illustrated in FIG. 9. Specifically, when the second connection member 22 tries to rotate in the second circumferential direction B2 relative to the first connection member 21, a tensile force in the circumferential direction B acts on the main body portion 61 of the deformation portion 58, but a bending moment rotating in the axial direction A hardly acts. Therefore, the bending moment hardly acts on the deformation portion 58 at the time of restricting the relative rotation of the first connection member 21 and the second connection member 22, and the breakage of the deformation portion 58 can be suppressed.

Figure 14:
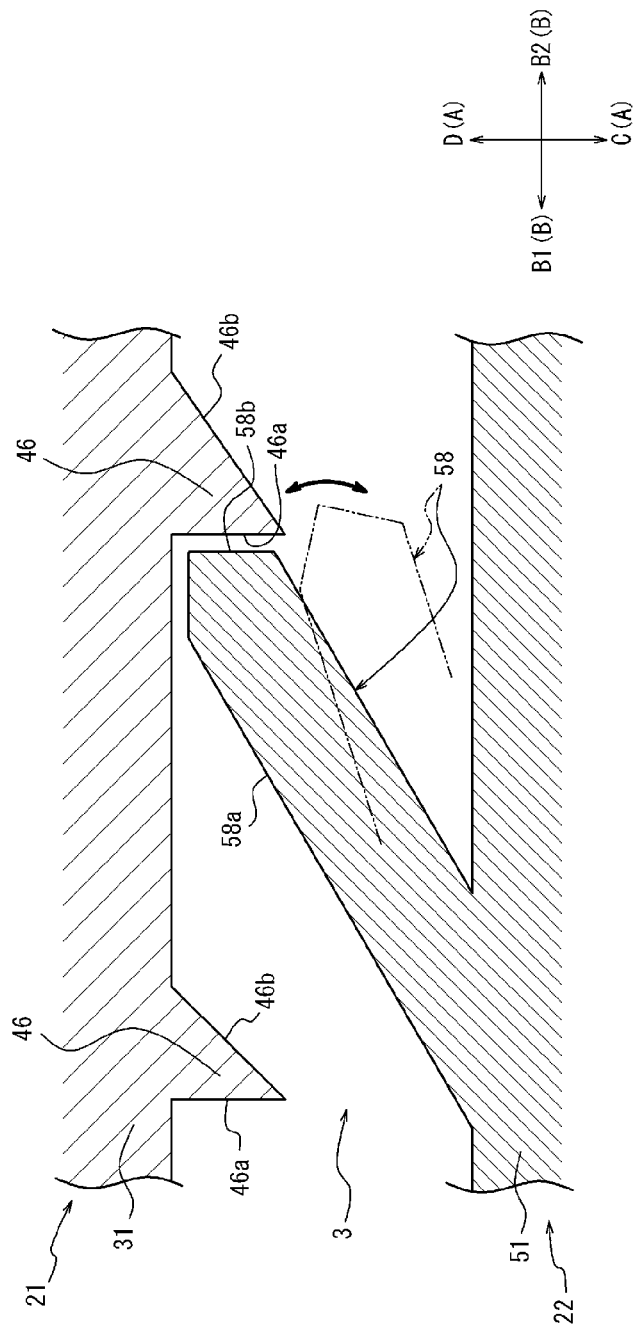
FIG. 14 is a view illustrating still another modification of the ratchet mechanism illustrated in FIG. 8.

FIG. 14 is a view illustrating another modification of the deformation portion 58. A projecting portion serving as the deformation portion 58 illustrated in FIG. 14 extends linearly to be inclined with respect to the axial direction A. When the deformation portion 58 is configured to extend linearly, the durability of the deformation portion 58 can be enhanced as compared with the configuration illustrated in FIG. 9. Specifically, when the second connection member 22 tries to rotate in the second circumferential direction B2 relative to the first connection member 21, the deformation portion 58 that is hardly broken can be realized.

Figure 15:
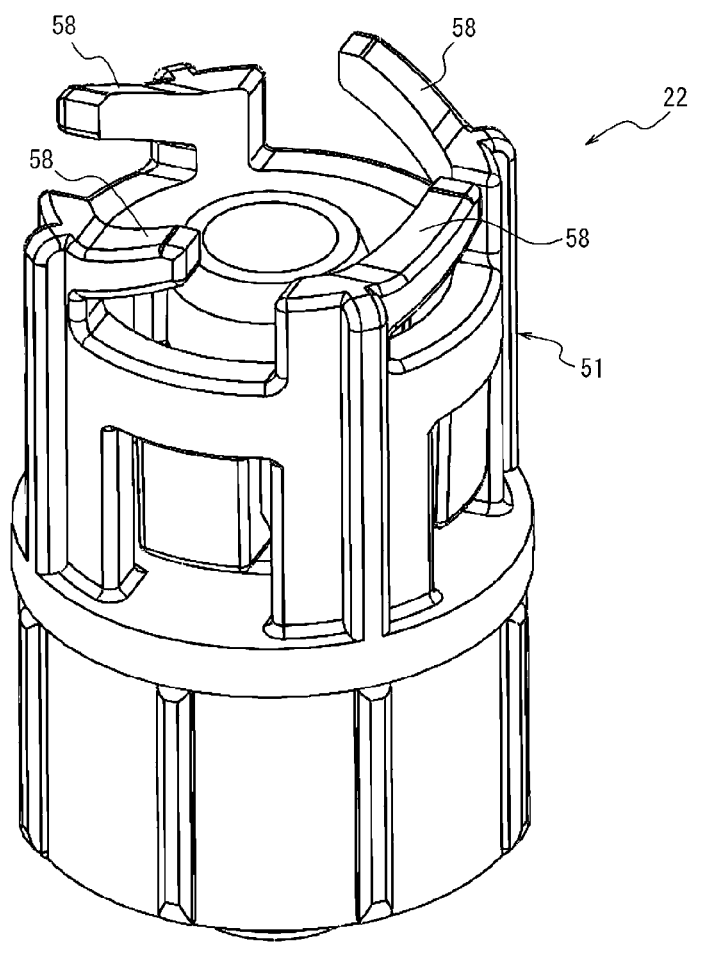
FIG. 15 is a perspective view illustrating a second connection member including a deformation portion illustrated in FIG. 14.

FIG. 15 is a perspective view illustrating the second connection member 22 including the deformation portion 58 illustrated in FIG. 14. Although four deformation portions 58 illustrated in FIG. 15 are provided at different positions in the circumferential direction B, the number thereof is not particularly limited, and may be one to three, or five or more.

Figure 11:
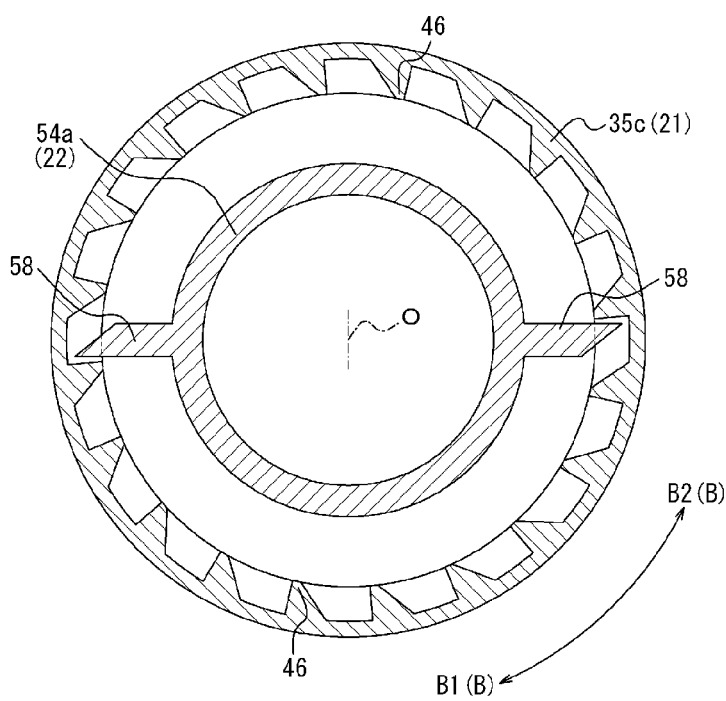
FIG. 11 is a view illustrating another modification of the ratchet mechanism illustrated in FIG. 8.

FIG. 11 is a schematic view illustrating another modification of the ratchet mechanism. FIG. 11 illustrates only a part of the configuration of the medical connector. In FIG. 11, the plurality of convex portions 46 are provided at a predetermined pitch along the circumferential direction B on the inner wall of the outer tubular portion 35*c* of the first connection member 21. In FIG. 11, a projecting portion serving as the deformation portion 58, which projects radially outward and is elastically deformable in the circumferential direction B, is provided on an outer wall of the connecting outer tubular portion 54a of the second connection member 22. The ratchet mechanism may include the convex portion 46 and the deformation portion 58 as illustrated in FIG. 11. Further, the convex portion 46 is provided on the first connection member 21 and the deformation portion 58 is provided on the second connection member 22 in FIGS. 1 to 11, but installation points of the convex portion 46 and the deformation portion 58 may be reversed. That is, it may be configured such that the first connection member 21 is provided with a deformation portion and the second connection member 22 is provided with a convex portion.

[Connecting Operation and Disconnecting Operation Between Medical Connector 100 and Medical Device]

Figure 12:
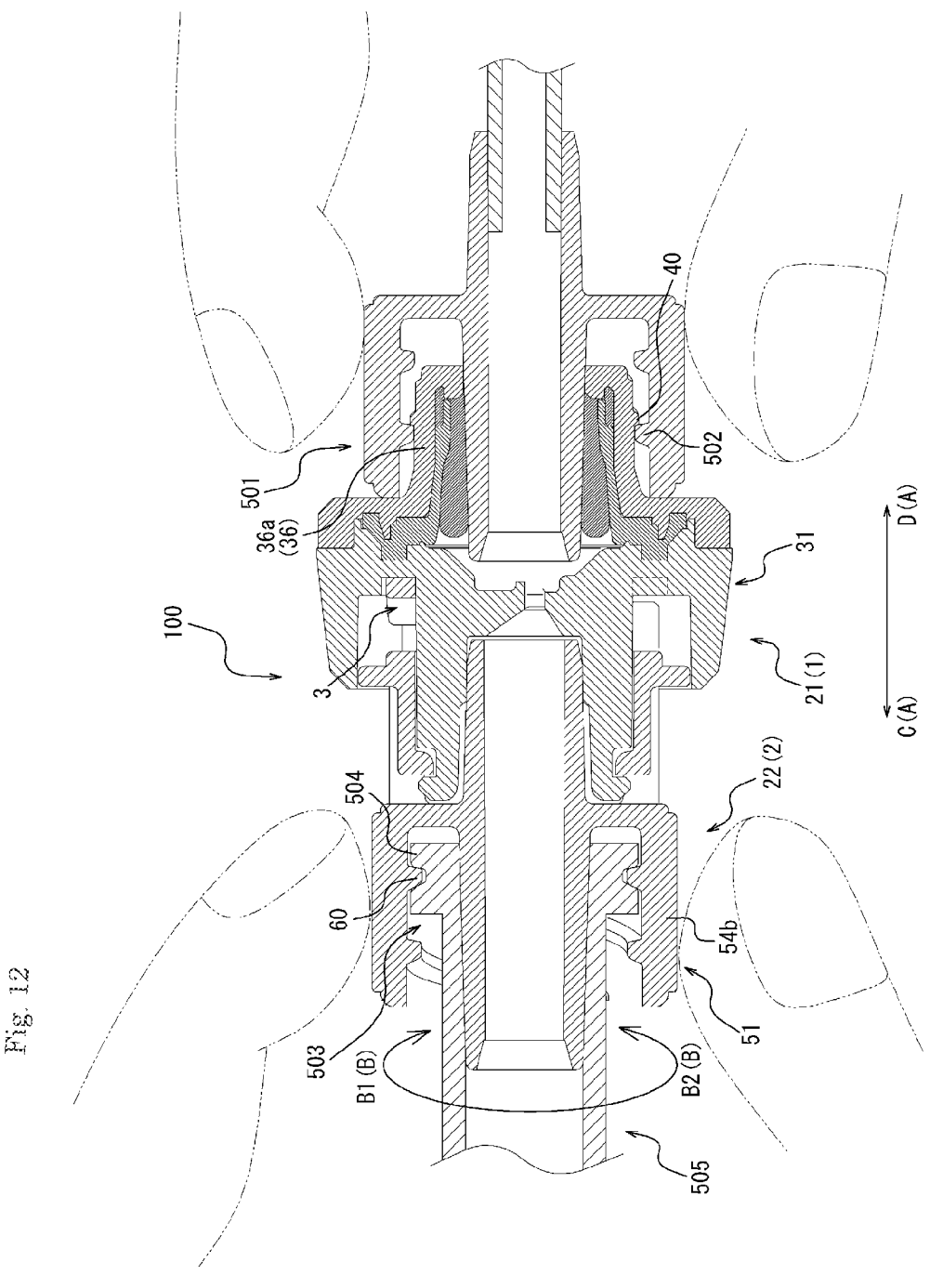
FIG. 12 is a cross-sectional view illustrating a state in which a first medical device is connected to a first connection section and a second medical device is connected to a second connection section in the medical connector illustrated in FIG. 1.

Next, a connecting operation and a disconnecting operation between the medical connector 100 of the present embodiment and a medical device will be described. FIG. 12 illustrates a state in which a lock-type male connector 501 conforming to ISO 80369-7 in 2016 serving as the first medical device is connected to the first connection section 1 of the medical connector 100 of the present embodiment. Further, FIG. 12 illustrates a state in which a medical tube 505 including a lock-type female connector portion 503 conforming to ISO 80369-7 in 2016 serving as the second medical device is connected to the second connection section 2 of the medical connector 100 of the present embodiment. However, a lock-type female connector conforming to ISO 80369-7 in 2016, which is attachable to and detachable from the medical tube 505, may be used as the second medical device.

As described above, the first connection member 21 constitutes the first connection section 1, and the second connection member 22 constitutes the second connection section 2 in the medical connector 100 of the present embodiment (see FIG. 1 and the like). As described above, the rotation control section 3 includes the ratchet mechanism formed of the first connection member 21 and the second connection member 22. The ratchet mechanism of the rotation control section 3 allows the second connection section 2 to rotate in the first circumferential direction B1 relative to the first connection section 1. Further, the ratchet mechanism of the rotation control section 3 restricts the second connection section 2 from rotating in the second circumferential direction B2, opposite to the first circumferential direction B1, relative to the first connection section 1.

As illustrated in FIG. 12, the first connection section 1 includes the male screw portion 40 that can be screwed with a female screw portion 502 of the lock-type male connector 501 serving as the first medical device. Specifically, the male screw portion 40 of the present embodiment is formed on the outer wall of the hollow tubular portion 36a of the top face cap 36 in the first housing 31 of the first connection member 21 constituting the first connection section 1 as described above (see FIG. 4 and the like).

As illustrated in FIG. 12, the male screw portion 40 is configured to be screwed with the female screw portion 502 of the lock-type male connector 501 by being rotated in the first circumferential direction B1 relative to the female screw portion 502 of the lock-type male connector 501.

With such a configuration, when connecting the female screw portion 502 of the lock-type male connector 501 to the first connection section 1 of the medical connector 100, a medical staff such as a doctor and a nurse can execute joining by screwing the medical connector 100 with the female screw portion 502 of the lock-type male connector 501 even in the state of gripping the second connection section 2 without gripping the first connection section 1. Specifically, a description will be given assuming a case where the medical staff grips the second connection section 2 with one hand and grips the lock-type male connector 501 with the other hand. In this case, when the second connection section 2 is rotated in the second circumferential direction B2 relative to the female screw portion 502 of the lock-type male connector 501, the first connection section 1 rotates together by the ratchet mechanism. Therefore, the first connection section 1 can be rotated in the second circumferential direction B2 relative to the female screw portion 502. Accordingly, the first connection section 1 and the female screw portion 502 of the lock-type male connector 501 can be connected by screwing.

Next, a description will be given assuming a state in which the first connection section 1 and the female screw portion 502 of the lock-type male connector 501 are connected by screwing. In this state, even if an unintended external force causing rotation in the first circumferential direction B1 acts on the second connection member 22 constituting the second connection section 2, the first connection section 1 and the second connection section 2 rotate relative to each other to idle by the ratchet mechanism of the rotation control section 3 Accordingly, the external force acting on the second connection member 22 to cause rotation in the first circumferential direction B1 is hardly transmitted to the threaded portion between the first connection section 1 and the female screw portion 502 of the lock-type male connector 501. That is, it becomes difficult for the first connection section 1 to rotate in the first circumferential direction B1 relative to the female screw portion 502. Accordingly, it is possible to suppress the connection state, obtained by screwing the first connection section 1 with the female screw portion 502 of the lock-type male connector 501, from being loosened by the unintended external force. Therefore, it is possible to suppress the connection state, obtained by screwing the first connection section 1 with the female screw portion 502 of the lock-type male connector 501, from being released by the unintended external force.

Further, in the state in which the first connection section 1 and the female screw portion 502 of the lock-type male connector 501 are connected by screwing, the medical staff can release the connection by causing relative rotation in the circumferential direction B while gripping the lock-type male connector 501 with one hand and gripping the first connection section 1 with the other hand. However, an erroneous operation for the purpose of disconnecting the connection at the same position is likely to occur. The erroneous operation referred to herein indicates an operation that the medical staff causes relative rotation in the circumferential direction B while gripping the lock-type male connector 501 with one hand and gripping the medical tube 505 connected to the second connection section 2 with the other hand, instead of the medical connector 100. With the medical connector 100 of the present embodiment, the first connection section 1 and the second connection section 2 idle due to the ratchet mechanism of the rotation control section 3 even if the above-described erroneous operation is performed. Therefore, the connection between the second connection section 2 and the male screw portion 504 of the lock-type female connector portion 503 of the medical tube 505 is not erroneously released. That is, it is possible to suppress disconnection at an unintended erroneous position.

Further, the second connection section 2 includes the female screw portion 60 as illustrated in FIG. 12. The female screw portion 60 can be screwed with the male screw portion 504 of the lock-type female connector portion 503 of the medical tube 505 serving as the second medical device. Specifically, the female screw portion 60 of the present embodiment is formed on the inner wall of the distal outer tubular portion 54b of the second housing 51 of the second connection member 22 constituting the second connection section 2 as described above (see FIG. 4 and the like).

As illustrated in FIG. 12, the female screw portion 60 is configured to be screwed with the male screw portion 504 of the lock-type female connector portion 503 by being rotated in the first circumferential direction B1 relative to the male screw portion 504 of the lock-type female connector portion 503 of the medical tube 505.

With such a configuration, when connecting the male screw portion 504 of the lock-type female connector portion 503 to the second connection section 2 of the medical connector 100, a medical staff such as a doctor and a nurse can execute joining by screwing the medical connector 100 with the male screw portion 504 of the lock-type female connector portion 503 in the medical tube 505 even in the state of gripping the first connection section 1 without gripping the second connection section 2. Specifically, a description will be given assuming a case where the medical staff grips the first connection section 1 with one hand and grips the medical tube 505 including the lock-type female connector portion 503 with the other hand. In this case, when the first connection section 1 is rotated in the first circumferential direction B1 relative to the male screw portion 504 of the lock-type female connector portion 503, the second connection section 2 rotates together by the ratchet mechanism. Therefore, the second connection section 2 can be rotated in the first circumferential direction B1 relative to the male screw portion 504. Accordingly, the second connection section 2 and the male screw portion 504 of the lock-type female connector portion 503 in the medical tube 505 can be connected by screwing.

Next, a description will be given assuming a state in which the second connection section 2 and the male screw portion 504 of the lock-type female connector portion 503 of the medical tube 505 are connected by screwing. In this state, even if an unintended external force causing rotation in the second circumferential direction B2 acts on the first connection member 21 constituting the first connection section 1, the first connection section 1 and the second connection section 2 rotate relative to each other to idle by the ratchet mechanism of the rotation control section 3. Accordingly, the external force acting on the first connection member 21 to cause rotation in the second circumferential direction B2 is hardly transmitted to the threaded portion between the second connection section 2 and the male screw portion 504 of the lock-type female connector portion 503. That is, it becomes difficult for the second connection section 2 to rotate in the second circumferential direction B2 with respect to the male screw portion 504. Accordingly, it is possible to suppress the connection state, obtained by screwing the second connection section 2 with the male screw portion 504 of the lock-type female connector portion 503, from being loosened by the unintended external force. Therefore, it is possible to suppress the connection state, obtained by screwing the second connection section 2 with the medical tube 505 including the male screw portion 504 of the lock-type female connector portion 503, from being released by the unintended external force.

Further, in the state in which the second connection section 2 and the male screw portion 504 of the lock-type female connector portion 503 in the medical tube 505 are connected by screwing, the medical staff can release the connection by causing relative rotation in the circumferential direction B while gripping the medical tube 505 including the lock-type female connector portion 503 with one hand and gripping the second connection section 2 with the other hand. However, an erroneous operation for the purpose of disconnecting the connection at the same position is likely to occur. The erroneous operation referred to herein indicates an operation that the medical staff causes relative rotation in the circumferential direction B while gripping the medical tube 505 including the female connector portion 503 of the lock type with one hand and gripping the lock-type male connector 501 connected to the first connection section 1 with the other hand, instead of the medical connector 100. With the medical connector 100 of the present embodiment, the first connection section 1 and the second connection section 2 idle due to the ratchet mechanism of the rotation control section 3 even if the above-described erroneous operation is performed. Therefore, the connection between the first connection section 1 and the female screw portion 502 of the lock-type male connector 501 is not erroneously released. That is, it is possible to suppress disconnection at an unintended erroneous position.

[Rotation Performance and Sealing Performance of Ratchet Mechanism of Medical Connector 100]

As illustrated in FIG. 4, the connecting inner tubular portion 52a serving as a second tubular portion of the second connection section 2 is inserted into the inner tubular portion 35a serving as a first tubular portion of the first connection section 1 in the medical connector 100 of the present embodiment.

As illustrated in FIG. 4, the inner wall of the inner tubular portion 35a serving as the first tubular portion and the outer wall of the connecting inner tubular portion 52a serving as the second tubular portion form the abutment region T2 only in each part of the inner tubular portion 35a and the connecting inner tubular portion 52a in the axial direction, in the insertion region T1. As described above, the insertion region T1 is a region in the axial direction (the same direction as the axial direction A in the present embodiment) where the inner tubular portion 35a and the connecting inner tubular portion 52a overlap in the radial direction. The abutment region T2 is a region in the axial direction where the inner peripheral face of the inner tubular portion 35a is in close contact with the outer peripheral face of the connecting inner tubular portion 52a. The second connection section 2 rotates in the first circumferential direction B1 relative to the first connection section 1 while sliding with respect to the first connection section 1 in the abutment region T2 described above.

In this manner, the abutment region T2 is only a part of the insertion region T1 in the axial direction of the inner tubular portion 35a and the connecting inner tubular portion 52a. Therefore, the sliding resistance when the inner tubular portion 35a and the connecting inner tubular portion 52a relatively rotate can be reduced as compared with the case where the abutment region exists over the entire insertion region. Accordingly, the relative rotation of the first connection section 1 and the second connection section 2 can be smoothly performed. A lubricant such as silicone oil may be interposed in the abutment region T2. With this configuration, the relative rotation of the first connection section 1 and the second connection section 2 can be performed even more smoothly.

In the present embodiment, a length of the abutment region T2 in the axial direction A is preferably ⅓ or less and more preferably ¼ or less, of the total length of the insertion region T1 in the axial direction A.

In the present embodiment, the taper angle of the proximal inner peripheral face 81 of the inner tubular portion 35a (see FIG. 7) with respect to the axial direction A and the taper angle of the distal base portion face 85a (see FIG. 7) of the distal outer peripheral face 85 of the connecting inner tubular portion 52a with respect to the axial direction A are made different in order to shorten the length of the abutment region T2 (see FIG. 4) in the axial direction A as described above. More specifically, the taper angle of the distal base portion face 85a (see FIG. 7) of the distal outer peripheral face 85 of the connecting inner tubular portion 52a with respect to the axial direction A is made larger than the taper angle of the proximal inner peripheral face 81 (see FIG. 7) of the inner tubular portion 35a with respect to the axial direction A. Alternatively, the length of the abutment region T2 in the axial direction A may be shortened by utilizing, for example, undercut fitting.

Further, the abutment region T2 in the present embodiment (see FIG. 4) is formed of the proximal inner peripheral face 81 of the inner tubular portion 35a of the first connection member 21 constituting the first connection section 1 (see FIG. 7) and the distal outer peripheral face 85 (see FIG. 7) of the connecting inner tubular portion 52a of the second connection member 22 constituting the second connection section 2, but is not limited to this configuration. The abutment region T2 may be formed of, for example, an inner peripheral face at another position of the inner tubular portion 35a and an outer peripheral face at another position or a distal face of the connecting inner tubular portion 52a.

Furthermore, the abutment region T2 is formed by inserting the connecting inner tubular portion 52a serving as the second tubular portion of the second connection section 2 into the inner tubular portion 35a serving as the first tubular portion of the first connection section 1 in the present embodiment as illustrated in FIG. 4, but is not limited to this configuration. The abutment region T2 may be formed, for example, by inserting the inner tubular portion serving as the second tubular portion of the first connection section 1 into the connecting inner tubular portion serving as the first tubular portion of the second connection section 2.

The abutment region T2 of the present embodiment is formed over the entire region in the circumferential direction (the same direction as the circumferential direction B in the present embodiment) of the inner tubular portion 35a serving as the first tubular portion and the connecting inner tubular portion 52a serving as the second tubular portion as described above. Accordingly, the first passage 1a of the first connection section 1 defined by the first connection member 21 and the second passage 2a of the second connection section 2 defined by the second connection member 22 are connected in a liquid-tight manner as described above.

[With Regard to Connection Configuration Between First Housing 31 and Second Housing 51]

As illustrated in FIG. 4, the annular groove 45 is formed on the outer wall of the inner tubular portion 35a serving as the first tubular portion of the first connection section 1. As illustrated in FIG. 4, the second connection section 2 includes the claw portion 57 that is located outside the inner tubular portion 35a of the first connection section 1 in the radial direction and fits into the annular groove 45.

That is, the first housing 31 of the first connection member 21 constituting the first connection section 1 and the second housing 51 of the second connection member 22 constituting the second connection section 2 are connected by fitting between the annular groove 45 and the claw portion 57 in the present embodiment.

As described above, the second connection section 2 includes the wall face 5. The wall face 5 abuts on the first connection section 1 to restrict the first connection section 1 from moving in the direction to be separated from the second connection section 2 along the axial direction A. In the present embodiment, the wall face 5 is constituted by the outer wall of the claw portion 57. More specifically, the wall face 5 of the present embodiment is constituted by an end face 57b1 of the locking projection 57b of the claw portion 57 on the side of the insertion direction C.

As described above, the first connection section 1 of the present embodiment includes the wall face 6. The wall face 6 abuts on the wall face 5 of the second connection section 2 to restrict the second connection section 2 from moving in the direction to be separated from the first connection section 1 along the axial direction A. In the present embodiment, the wall face 6 is constituted by a groove wall of the annular groove 45. More specifically, the wall face 6 of the present embodiment is constituted by a groove wall 45a1 of the annular groove 45 on the side of the removal direction D opposite to the insertion direction C.

Further, the second connection section 2 of the present embodiment includes a wall face 7. The wall face 7 abuts on the first connection section 1 to restrict the first connection section 1 from moving in a direction to approach the second connection section 2 along the axial direction A. Hereinafter, the wall face 5 is described as a "first wall face 5" and the wall face 7 is described as a "second wall face 7" in order to distinguish the wall face 5 and the wall face 7 of the second connection section 2 for convenience of description. In the present embodiment, the second wall face 7 of the second connection section 2 is constituted by the outer wall of the claw portion 57. More specifically, the second wall face 7 of the second connection section 2 of the present embodiment is constituted by an end face 57b2 of the locking projection 57b of the claw portion 57 on the side of the removal direction D opposite to the insertion direction C.

Further, the first connection section 1 of the present embodiment includes a wall face 8. The wall face 8 abuts on the second wall face 7 of the second connection section 2 to restrict the second connection section 2 from moving in a direction to approach the first connection section 1 along the axial direction A. Hereinafter, the wall face 6 is described as a "first wall face 6" and the wall face 8 is described as a "second wall face 8" in order to distinguish the wall face 6 and the wall face 8 of the first connection section 1 for convenience of description. In the present embodiment, the second wall face 8 of the first connection section 1 is constituted by a groove wall of the annular groove 45. More specifically, the second wall face 8 of the first connection section 1 of the present embodiment is constituted by a groove wall 45a2 of the annular groove 45 on the side of the insertion direction C.

The groove wall 45a1 of the annular groove 45 serving as the first wall face 6 of the first connection section 1 and the end face 57b1 of the locking projection 57b of the claw portion 57 serving as the first wall face 5 of the second connection section 2 abut on each other to come into contact in the axial direction A. Accordingly, the first connection section 1 and the second connection section 2 in the connected state are restricted from moving to be separated from each other in the axial direction A. Therefore, the connection state between the first connection section 1 and the second connection section 2 is maintained. In other words, the state in which the groove wall 45a1 of the annular groove 45 serving as the first wall face 6 of the first connection section 1 and the end face 57b1 of the locking projection 57b of the claw portion 57 serving as the first wall face 5 of the second connection section 2 abut on each other to come into contact in the axial direction A is the above-described separation-restricted state.

In the above-described separation-restricted state, the rotation control section 3 allows the second connection section 2 to move in the first circumferential direction B1 and restricts the second connection section 2 from moving in the second circumferential direction B2, relative to the first connection section 1.

Further, the groove wall 45*a*2 of the annular groove 45 serving as the second wall face 8 of the first connection section 1 and the end face 57*b*2 of the locking projection 57*b* of the claw portion 57 serving as the second wall face 7 of the second connection section 2 abut on each other to come into contact in the axial direction A. Accordingly, the first connection section 1 and the second connection section 2 in the connected state are restricted from moving to approach each other in the axial direction A. In other words, the state in which the groove wall 45*a*2 of the annular groove 45 serving as the second wall face 8 of the first connection section 1 and the end face 57*b*2 of the locking projection 57*b* of the claw portion 57 serving as the second wall face 7 of the second connection section 2 abut on each other to come into contact in the axial direction A is an approach-restricted state.

Even in the above-described approach-restricted state, the rotation control section 3 of the present embodiment allows the second connection section 2 to move in the first circumferential direction B1 and restricts the second connection section 2 from moving in the second circumferential direction B2, relative to the first connection section 1.

That is, the rotation control section 3 of the present embodiment allows the second connection section 2 to rotate in the first circumferential direction B1 relative to the first connection section 1 in both the states of the above-described separation-restricted state and approach-restricted state. Further, the rotation control section 3 of the present embodiment restricts the second connection section 2 from rotating in the second circumferential direction B2 relative to the first connection section 1 in both the states of the above-described separation-restricted state and approach-restricted state. In other words, the rotation control section 3 of the present embodiment is configured to be capable of executing the above-described rotation control constantly in the connection state by providing the above-described separation-restricted state and the approach-restricted state. More specifically, the state in which the convex portion 46 (see FIG. 6 and the like) and the deformation portion 58 (see FIG. 5 and the like) are arranged at the overlapping positions in the circumferential direction B is maintained by providing the above-described separation-restricted state in the present embodiment. Further, excessive interference between the convex portion 46 (see FIG. 6 and the like) and the deformation portion 58 (see FIG. 5 and the like) is suppressed by providing the above-described approach-restricted state in the present embodiment. That is, it is possible to suppress malfunction of the rotation control section 3 in which the deformation portion 58 (see FIG. 5 and the like) excessively presses the convex portion 46 (see FIG. 6 and the like) to prevent the second connection section 2 from rotating in the first circumferential direction B1 relative to the first connection section 1.

Finally, an infusion set 600 including the medical connector 100 of the present embodiment will be described with reference to FIG. 13.

Figure 13:
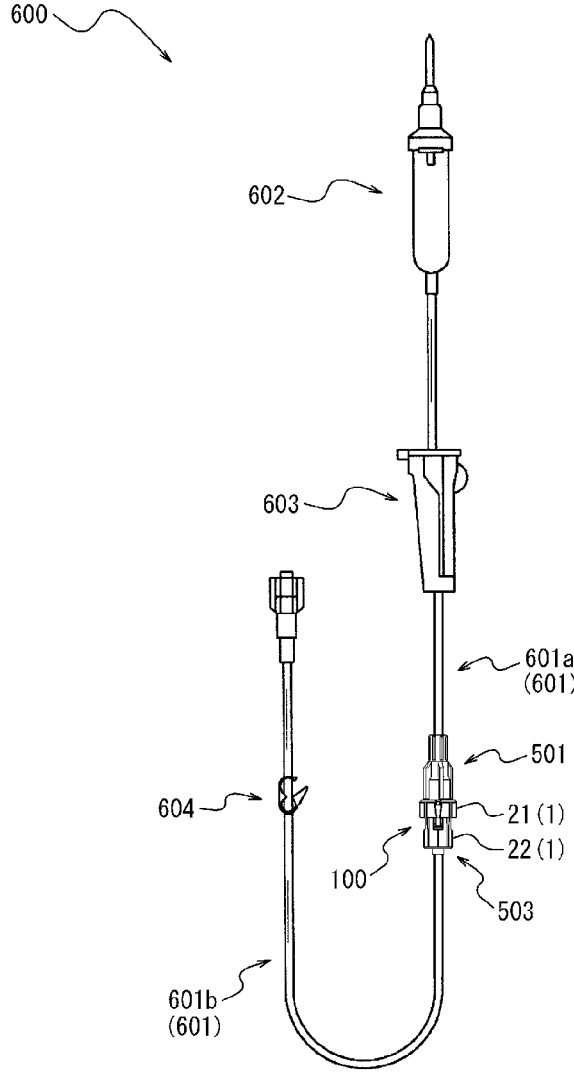
FIG. 13 is a view illustrating an infusion set including the medical connector illustrated in FIG. 1.

The infusion set 600 constitutes an infusion line connecting an infusion holder such as an infusion bag (not illustrated in FIG. 13) to an indwelling needle (also not illustrated in FIG. 13). Specifically, the infusion set 600 includes a plurality of medical tubes 601, a drip chamber 602, an adjusting clamp 603, a closing clamp 604, and the medical connector 100. The plurality of medical tubes 601 illustrated in FIG. 13 include a first medical tube 601*a* and a second medical tube 601*b*. The drip chamber 602 enables visual confirmation of a flow rate of an infusion agent supplied from the infusion holder. The adjusting clamp 603 can change the flow rate of the infusion agent in the medical tube 601 to a plurality of states. The closing clamp 604 can close the medical tube 601. The medical connector 100 connects the plurality of medical tubes 601 to each other.

The lock-type male connector 501 serving as the first other medical device illustrated in FIG. 12 is attached to a distal end portion of the first medical tube 601*a*. The first medical tube 601*a* and the lock-type male connector 501 may be connected undetachably or detachably.

The second medical tube 601*b* serving as the second medical device includes the lock-type female connector portion 503 illustrated in FIG. 12 in a proximal end portion thereof. However, a lock-type female connector attached to the proximal end portion of the second medical tube 601*b* serving as the second medical device may be used. In such a case, the lock-type female connector may be connected to the second medical tube 601*b* undetachably or detachably.

As illustrated in FIG. 13, the first connection section 1, located on the proximal end side (on the upstream side of a passage of the infusion line) in the medical connector 100, is connected to the lock-type male connector 501. As illustrated in FIG. 13, the second connection section 2, located on the distal end side (on the downstream side of the passage of the infusion line) in the medical connector 100, is connected to the lock-type female connector portion 503 of the second medical tube 601*b*. In this manner, the medical connector 100 connects a passage in the first medical tube 601*a* and a passage in the second medical tube 601*b* in a liquid-tight manner through the first passage 1*a* (see FIG. 4) and the second passage 2*a* (see FIG. 4).

The infusion set 600 illustrated in FIG. 13 is an example, and is not limited to the configuration illustrated in FIG. 13 as long as including at least one medical tube 601 and the medical connector 100.

The medical connector according to the present disclosure is not limited to the specific configuration described in the above embodiment, and various modifications and changes can be made without departing from the scope of the claims. For example, the first connection section 1 is provided with the male screw portion 40 (see FIG. 4 and the like), and the second connection section 2 is provided with the female screw portion 60 (see FIG. 4 and the like) in the medical connector 100 of the above-described embodiment. However, the medical connector may be configured such that, for example, the first connection section 1 is provided with a female screw portion and the second connection section 2 is provided with a male screw portion. Further, the medical connector may adopt, for example, a configuration in which a male screw portion is provided in the first connection section 1 and the second connection section 2, or a configuration in which a female screw portion is provided in the first connection section 1 and the second connection section 2.

Further, the first connection section 1 and the second connection section 2 are configured to be connected to medical devices by screwing in the medical connector 100 of the above-described embodiment, but may be configured to be connected to medical devices by utilizing the rotating operation in the circumferential direction B that is rotationally controlled by the rotation control section 3 without being limited to the screwing. However, it is preferable to use screwing as in the medical connector 100 of the above-described embodiment. Then, the connecting operation with the medical device is facilitated, and the rotation control performed by the rotation control section 3 is also easily realized.

Further, the separation and approach between the first connection section 1 and the second connection section 2 in the axial direction A are restricted by the annular groove 45 (see FIG. 4 and the like) and the claw portion 57 (see FIG. 4 and the like) in the medical connector 100 of the above-described embodiment, but the separation and approach between the first connection section 1 and the second connection section 2 in the axial direction A may be restricted using other configurations. However, the above-described restriction on the separation and approach can be realized with a simple configuration if the configuration in which the separation and approach between the first connection section 1 and the second connection section 2 in the axial direction A by the annular groove 45 (see FIG. 4 and the like) and the claw portion 57 (see FIG. 4 and the like) is adopted as in the medical connector 100 of the present embodiment.

Furthermore, the example (see FIG. 12) in which the lock-type male connector 501 conforming to ISO 80369-7 in 2016 is connected to the first connection section 1 of the medical connector 100 is illustrated in the above-described embodiment, but the medical device, such as a medical tube provided with a lock-type male connector portion conforming to the ISO 80369-7 in 2016 in an end portion, may be connected without being limited to such a configuration.

Figure 16:
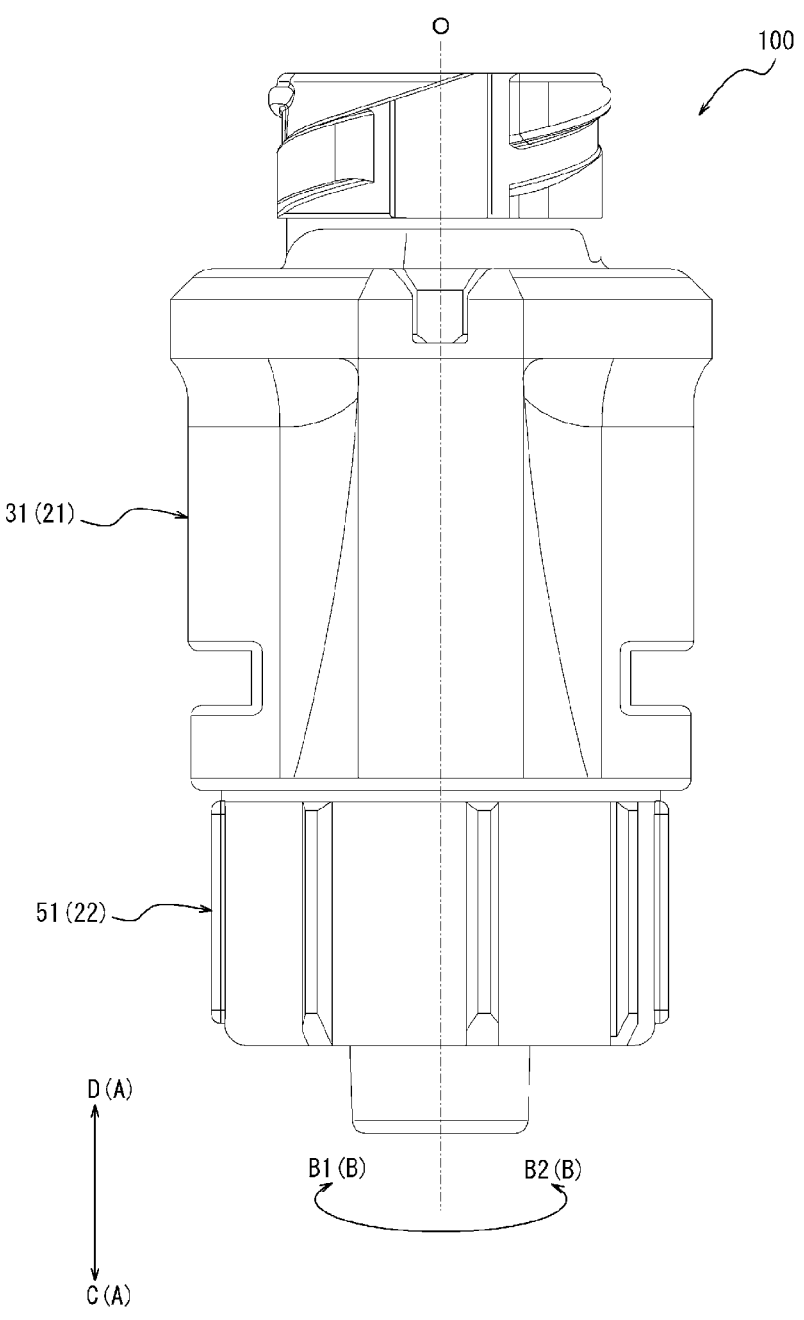
FIG. 16 is a side view of a modification of the medical connector illustrated in FIG. 1 as viewed from the side surface.
Figure 17:
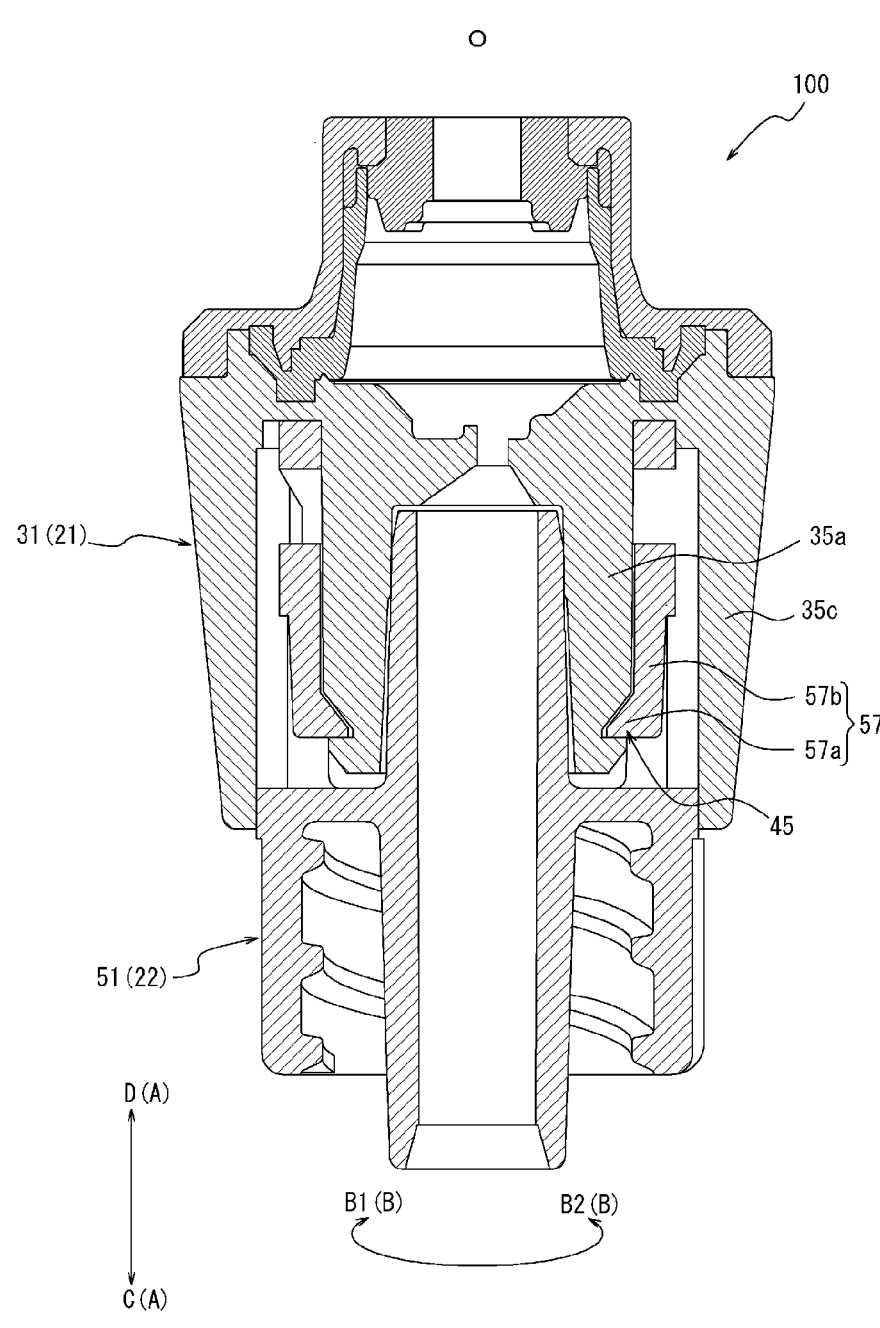
FIG. 17 is a cross-sectional view of the medical connector illustrated in FIG. 16 in the same cross section as FIG. 4.

In the above-described embodiment, the outer tubular portion 35*c* of the first housing 31 of the medical connector 100 does not completely cover the radially outer side of the claw portion 57 of the second housing 51. On the other hand, a length of the outer tubular portion 35*c* of the first housing 31 in the axial direction A may be made longer than that in the configuration illustrated in FIG. 4 and the like as illustrated in FIGS. 16 and 17. Then, a proportion occupied by the first housing 31 increases and a proportion occupied by the second housing 51 decreases on an outer surface exposed to the outside of the medical connector 100. Therefore, when an operator such as a medical staff detaches the first medical device 501 (see FIG. 12) from the first connection member 21, it becomes easy to grip the first housing 31 of the first connection member 21. As a result, it is possible to suppress the second housing 51 of the second connection member 22 from being erroneously gripped. As illustrated in FIG. 17, the outer tubular portion 35*c* is longer than the inner tubular portion 35*a*. More specifically, a distal end of the outer tubular portion 35*c* in the insertion direction C is located to be closer to the insertion direction C than a distal end of the inner tubular portion 35*a* in the insertion direction C.

In FIGS. 16 and 17, the outer tubular portion 35*c* covers the radially outer side of the claw portion 57 of the second housing 51. With such a configuration, it is possible to suppress an operator such as a medical staff from erroneously pressing the claw portion 57 from the outer side to the inner side in the radial direction at the time of operating the medical connector 100. Accordingly, it is possible to suppress the claw portion 57 from being pressed against a groove bottom of the annular groove 45 to increase a frictional force therebetween. As a result, it is possible to suppress generation of a problem that the ratchet mechanism of the medical connector 100 does not operate normally.

The present disclosure relates to a medical connector.

What is claimed is:

1. A medical connector defining a connector passage and comprising:

a first connection section that defines a first passage of the connector passage, the first connection section comprising a first tubular portion;

a second connection section that defines a second passage of the connector passage, the second passage communicating with the first passage, the second connection section comprising a second tubular portion inserted into the first tubular portion; and a rotation control section that controls relative rotation of the first connection section and the second connection section in a connection state; wherein:

the second connection section comprises a wall face configured to abut on the first connection section to restrict the first connection section from moving in a direction to be separated from the second connection section along an axis of the first passage and the second passage;

in a state in which the wall face abuts on the first connection section, the rotation control section allows the second connection section to rotate relative to the first connection section in a first circumferential direction about the axis and restricts the second connection section from rotating relative to the first connection section in a second circumferential direction opposite to the first circumferential direction;

the first connection section is connectable to a first medical device using a rotating operation in the second circumferential direction and is disconnectable from the first medical device using a rotating operation in the first circumferential direction;

each of an inner surface of the first tubular portion and an outer surface of the second tubular portion is tapered;

the tapered inner surface of the first tubular portion directly contacts the tapered outer surface of the second tubular portion in an abutment region along an axial direction in an insertion region where the first tubular portion and the second tubular portion overlap in a radial direction, wherein the abutment region is directly exposed to the connector passage; and the second connection section is configured to rotate in the first circumferential direction relative to the first connection section while sliding with respect to the first connection section in the abutment region.

2. The medical connector according to claim 1, wherein:

in the abutment region, the tapered inner surface of the first tubular portion directly contacts the tapered outer surface of the second tubular portion over an entire circumferential region of the first tubular portion and an entire circumferential region of the second tubular portion.

3. The medical connector according to claim 1, wherein:

the first connection section comprises a male screw portion that is screwable with a female screw portion of the first medical device; and the male screw portion is configured to screw with the female screw portion of the first medical device by being rotated in the second circumferential direction relative to the female screw portion of the first medical device.

4. The medical connector according to claim 1, wherein:

the second connection section is connectable to a second medical device using a rotating operation in the first circumferential direction and is disconnectable from the second medical device using a rotating operation in the second circumferential direction.

5. The medical connector according to claim 4, wherein:

the second connection section comprises a female screw portion that is screwable with a male screw portion of the second medical device; and the female screw portion is configured to screw with the male screw portion of the second medical device by being rotated in the first circumferential direction relative to the male screw portion of the second medical device.

6. The medical connector according to claim 1, comprising:

a first housing that forms at least a part of the first connection section; and a second housing that forms at least a part of the second connection section; wherein:

the rotation control section comprises a ratchet mechanism comprising part of the first housing and part of the second housing.

7. The medical connector according to claim 1, wherein:

an annular groove is formed on an outer wall of the first tubular portion;

the second connection section comprises a claw portion that is located on an outside of the first tubular portion of the first connection section in the radial direction and fits into the annular groove; and the wall face is constituted by a groove wall of the annular groove or an outer wall of the claw portion.

8. The medical connector according to claim 7, wherein:

the first connection section further comprises a support portion that extends outward from the first tubular portion and an outer tubular portion extending from the support portion; and the outer tubular portion of the first connection section extends distally from the support portion such that part of the claw portion is located between the first tubular portion and the outer tubular portion in the radial direction.

9. The medical connector according to claim 8, wherein the outer tubular portion is monolithic with the support portion and the first tubular portion.

10. A method comprising:

providing a medical connector defining a connector passage and comprising:

a first connection section that defines a first passage of the connector passage, the first connection section comprising a first tubular portion, a second connection section that defines a second passage of the connector passage, the second passage communicating with the first passage, the second connection section comprising a second tubular portion inserted into the first tubular portion, and a rotation control section that controls relative rotation of the first connection section and the second connection section in a connection state, wherein:

the second connection section comprises a wall face configured to abut on the first connection section to restrict the first connection section from moving in a direction to be separated from the second connection section along an axis of the first passage and the second passage, in a state in which the wall face abuts on the first connection section, the rotation control section allows the second connection section to rotate relative to the first connection section in a first circumferential direction about the axis and restricts the second connection section from rotating relative to the first connection section in a second circumferential direction opposite to the first circumferential direction, each of an inner surface of the first tubular portion and an outer surface of the second tubular portion is tapered, the tapered inner surface of the first tubular portion directly contacts the tapered outer surface of the second tubular portion in an abutment region along an axial direction in an insertion region where the first tubular portion and the second tubular portion overlap in a radial direction, wherein the abutment region is directly exposed to the connector passage, and the second connection section is configured to rotate in the first circumferential direction relative to the first connection section while sliding with respect to the first connection section in the abutment region; and connecting the first connection section to a first medical device by rotating the first connection section in the second circumferential direction.

11. A medical connector comprising:

a first connection member comprising:

a first housing comprising:

a substantially cylindrical inner tubular portion that defines a first passage and comprises an annular groove having a wall face, an annular support portion comprising a plurality of convex portions located at a lower face of the annular support portion, and a substantially cylindrical outer tubular portion, and a valve body attached to the first housing;

a second connection member comprising:

a second housing comprising:

a substantially cylindrical inner tubular portion defining a second passage communicating with the first passage, the substantially cylindrical inner tubular portion of the second housing inserted into the substantially cylindrical inner tubular portion of the first housing, an annular flange, and a substantially cylindrical outer tubular portion comprising:

a connecting outer tubular portion comprising:

a projecting portion configured to fit into a recess between the convex portions of the annular support portion of the first connection member, such that the projecting portion and the convex portions form a ratching mechanism, and a claw portion having a wall face, and a distal outer tubular portion comprising a female screw portion; wherein:

the wall face of the annular groove is configured to abut on the wall face of the claw portion to restrict the first connection member from moving in a direction to be separated from the second connection member along an axis of the first passage and the second passage;

in a state in which the wall face of the annular groove abuts on the wall face of the claw portion, the second connection member is able to rotate relative to the first connection member in a first circumferential direction about the axis, the second connection member is retricted from rotating relative to the first connection member in a second circumferential direction opposite to the first circumferential direction; and the first connection member is connectable to a first medical device using a rotating operation in the second circumferential direction and is disconnectable from the first medical device using a rotating operation in the first circumferential direction;

each of an inner surface of the substantially cylindrical inner tubular portion of the first housing and an outer surface of the substantially cylindrical inner tubular portion of the second housing is tapered;

each of the tapered inner surface of the substantially cylindrical inner tubular portion of the first housing and the tapered outer surface of the substantially cylindrical inner tubular portion of the second housing comprises an abutment region along an axial direction in an insertion region where the substantially cylindrical inner tubular portion of the first housing and the substantially cylindrical inner tubular portion of the second housing overlap in a radial direction; and the second connection member is configured to rotate in the first circumferential direction relative to the first connection member while sliding with respect to the first connection member in the abutment region.

\*　\*　\*　\*　\*